United States Patent
Ellman et al.

(10) Patent No.: US 12,426,964 B2
(45) Date of Patent: Sep. 30, 2025

(54) TIME-SPACED ROBOTIC REFERENCE FRAMES

(71) Applicant: Mazor Robotics Ltd., Caesarea (IL)

(72) Inventors: Aviv Ellman, Caesarea (IL); Dany Junio, Caesarea (IL); Katherine M. Puckett, Louisville, CO (US)

(73) Assignee: Mazor Robotics Ltd., Caesarea (IL)

( * ) Notice: Subject to any disclaimer, the term of this patent is extended or adjusted under 35 U.S.C. 154(b) by 293 days.

(21) Appl. No.: 18/003,147

(22) PCT Filed: Jun. 30, 2021

(86) PCT No.: PCT/IL2021/050804
§ 371 (c)(1),
(2) Date: Dec. 22, 2022

(87) PCT Pub. No.: WO2022/003687
PCT Pub. Date: Jan. 6, 2022

(65) Prior Publication Data
US 2023/0255699 A1    Aug. 17, 2023

Related U.S. Application Data

(60) Provisional application No. 63/046,393, filed on Jun. 30, 2020.

(51) Int. Cl.
*A61B 34/30*      (2016.01)
*A61B 34/00*      (2016.01)
(Continued)

(52) U.S. Cl.
CPC .............. *A61B 34/30* (2016.02); *A61B 34/20* (2016.02); *A61B 2034/2059* (2016.02); *A61B 2034/305* (2016.02)

(58) Field of Classification Search
CPC . A61B 34/30; A61B 34/20; A61B 2034/2059; A61B 2034/305; A61B 34/74;
(Continued)

(56) References Cited

U.S. PATENT DOCUMENTS

| 7,781,724 B2 | 8/2010 | Childers et al. |
| 7,907,166 B2 | 3/2011 | Lamprecht et al. |

(Continued)

FOREIGN PATENT DOCUMENTS

| CN | 100496429 | 6/2009 |
| CN | 107533634 | 1/2018 |

(Continued)

OTHER PUBLICATIONS

"Robotic Assisted Systems," Intuitive Surgical, Jul. 2019, 5 pages.
(Continued)

*Primary Examiner* — Jaime Figueroa
(74) *Attorney, Agent, or Firm* — Sheridan Ross P.C.

(57) ABSTRACT

A robotic navigation system includes a robot base (140); a robotic arm (144) comprising a proximal portion secured to the robot base, a distal portion movable relative to the proximal portion, and a tracking marker (156) secured to the robotic arm proximate the distal portion; at least one processor; a navigation system including a tracking marker sensor configured to identify positions of the tracking marker in a first coordinate space; and a memory. The memory stores instructions that cause the at least one processor to: cause the robotic arm (144) to move to a plurality of different poses; receive information relating to a position of the tracking marker (156) in a second coordinate space when the robotic arm is in each of the plurality of different poses; and compare the positions of the tracking marker in the first coordinate space to the positions of the tracking marker in the second coordinate space.

24 Claims, 7 Drawing Sheets

(51) Int. Cl.
  *A61B 34/20* (2016.01)
  *B25J 13/08* (2006.01)
(58) Field of Classification Search
  CPC .......... A61B 90/96; A61B 2017/00119; A61B 2017/00725; A61B 2034/2055; A61B 2034/2065; A61B 2090/067; A61B 2090/0818; A61B 2090/3945; B25J 13/089
  USPC ................. 700/245–264; 318/568.11–568.25
  See application file for complete search history.

(56) References Cited

U.S. PATENT DOCUMENTS

| | | | |
|---|---|---|---|
| 8,108,072 B2 | 1/2012 | Zhao et al. | |
| 8,392,022 B2 | 3/2013 | Ortmaier et al. | |
| 8,409,098 B2 | 4/2013 | Olson | |
| 9,050,728 B2 | 6/2015 | Ban et al. | |
| 9,211,164 B2 | 12/2015 | Moctezuma de la Barrera et al. | |
| 9,259,276 B2 | 2/2016 | Mintz et al. | |
| 9,259,282 B2 | 2/2016 | Azizian et al. | |
| 9,307,894 B2 | 4/2016 | von Grunberg et al. | |
| 9,402,689 B2 | 8/2016 | Prisco et al. | |
| 9,687,307 B2 | 6/2017 | Wu | |
| 9,734,589 B2 * | 8/2017 | Yu | G06T 7/248 |
| 9,767,608 B2 | 9/2017 | Lee et al. | |
| 9,969,090 B2 | 5/2018 | Warashina et al. | |
| 10,028,788 B2 | 7/2018 | Kang | |
| 10,165,981 B2 | 1/2019 | Schoepp | |
| 10,231,791 B2 | 3/2019 | LeBoeuf, II et al. | |
| 10,299,880 B2 | 5/2019 | Ramirez Luna et al. | |
| 10,368,054 B2 | 7/2019 | Panescu et al. | |
| 10,668,625 B2 | 6/2020 | Kuroda et al. | |
| 11,116,576 B2 * | 9/2021 | Theodore | A61B 34/20 |
| 11,298,196 B2 * | 4/2022 | Crawford | A61B 90/11 |
| 11,864,839 B2 * | 1/2024 | Decker | A61B 34/10 |
| 2003/0059097 A1 * | 3/2003 | Abovitz | A61B 6/12 382/294 |
| 2007/0106307 A1 | 5/2007 | Bodduluri et al. | |
| 2009/0076655 A1 | 3/2009 | Blondel et al. | |
| 2010/0168562 A1 | 7/2010 | Zhao et al. | |
| 2011/0087238 A1 | 4/2011 | Wang et al. | |
| 2013/0274921 A1 | 10/2013 | Aiso | |
| 2014/0179997 A1 | 6/2014 | Grunberg et al. | |
| 2014/0253684 A1 | 9/2014 | Kumar et al. | |
| 2014/0288710 A1 * | 9/2014 | Ikenaga | B25J 9/1692 901/47 |
| 2014/0330114 A1 * | 11/2014 | Navab | A61B 6/037 600/424 |
| 2015/0025683 A1 | 1/2015 | Amano | |
| 2015/0209119 A1 * | 7/2015 | Theodore | A61B 90/39 600/424 |
| 2016/0015468 A1 * | 1/2016 | Piron | A61B 5/064 600/424 |
| 2016/0256225 A1 * | 9/2016 | Crawford | A61B 90/98 |
| 2017/0245944 A1 | 8/2017 | Crawford et al. | |
| 2017/0258535 A1 * | 9/2017 | Crawford | B25J 15/0441 |
| 2017/0265774 A1 * | 9/2017 | Johnson | A61B 34/32 |
| 2018/0014888 A1 * | 1/2018 | Bonny | A61B 34/20 |
| 2018/0055577 A1 | 3/2018 | Barral et al. | |
| 2018/0064497 A1 | 3/2018 | Hussain et al. | |
| 2018/0140223 A1 * | 5/2018 | Kheradpir | A61B 34/20 |
| 2018/0147018 A1 * | 5/2018 | Crawford | A61B 17/7035 |
| 2018/0185100 A1 * | 7/2018 | Weinstein | A61B 34/20 |
| 2018/0214221 A1 * | 8/2018 | Crawford | A61B 17/00 |
| 2018/0256264 A1 * | 9/2018 | McLachlin | A61B 5/0035 |
| 2018/0296283 A1 * | 10/2018 | Crawford | G06T 3/02 |
| 2019/0000561 A1 * | 1/2019 | Decker | A61F 2/46 |
| 2019/0000569 A1 | 1/2019 | Crawford et al. | |
| 2019/0000571 A1 * | 1/2019 | Johnson | A61B 34/20 |
| 2019/0029765 A1 * | 1/2019 | Crawford | A61B 90/361 |
| 2019/0038366 A1 * | 2/2019 | Johnson | A61B 90/98 |
| 2019/0117313 A1 * | 4/2019 | Crawford | A61B 34/70 |
| 2019/0357986 A1 * | 11/2019 | Morgan | A61B 17/88 |
| 2019/0374299 A1 | 12/2019 | Peine | |
| 2019/0380794 A1 * | 12/2019 | Al Jewad | A61B 34/20 |
| 2019/0388161 A1 * | 12/2019 | Cicchini | A61B 90/11 |
| 2019/0388164 A1 * | 12/2019 | Gruionu | A61B 34/20 |
| 2020/0015806 A1 | 1/2020 | Scheib et al. | |
| 2020/0038116 A1 | 2/2020 | Toporek et al. | |
| 2020/0170730 A1 * | 6/2020 | Cameron | A61B 34/30 |
| 2020/0222122 A1 | 7/2020 | Snyder et al. | |
| 2020/0222127 A1 | 7/2020 | Snyder et al. | |
| 2020/0261160 A1 | 8/2020 | Peine et al. | |

FOREIGN PATENT DOCUMENTS

| | | |
|---|---|---|
| CN | 109551518 | 4/2019 |
| CN | 110834333 | 2/2020 |
| CN | 110897717 | 3/2020 |
| CN | 111317572 | 6/2020 |
| EP | 1096268 | 12/2006 |
| EP | 2594197 | 5/2013 |
| EP | 2783814 A2 | 10/2014 |
| EP | 2996615 | 1/2019 |
| EP | 3476358 | 5/2019 |
| EP | 3212104 | 11/2019 |
| EP | 3613544 A1 | 2/2020 |
| WO | WO 95/01757 | 1/1995 |
| WO | WO 2017/147596 | 8/2017 |
| WO | WO 2018/081136 A2 | 5/2018 |
| WO | WO 2019/071189 | 4/2019 |
| WO | WO 2020/016312 | 1/2020 |

OTHER PUBLICATIONS

Abdelaal et al. "A multi-camera, multi-view system for training and skill assessment for robot-assisted surgery," International Journal of Computer Assisted Radiology and Surgery, May 2020, vol. 15, pp. 1369-1377.
Boctor et al. "A Dual-Armed Robotic System for Intraoperative Ultrasound Guided Hepatic Ablative Therapy: A Prospective Study," IEEE, Proceedings of the 2004 IEEE International Conference on Robotics & Automation, New Orleans, LA, Apr. 2004, pp. 2517-2522.
He et al. "A Multi-Function Force Sensing Instrument for Variable Admittance Robot Control in Retinal Microsurgery," 2014 IEEE International Conference on Robotics and Automation (ICRA), 2014, pp. 1411-1418.
Joskowicz "Computer-aided surgery meets predictive, preventive, and personalized medicine," EPMA Journal, 2017, vol. 8, 4 pages.
Khandalavala "Emerging surgical robotic technology: a progression toward microbots," Annals of Laparoscopic and Endoscopic Surgery, Jan. 2020, vol. 5, Article 3, 18 pages.
Kim et al. "Robot-Assisted Cardiac Surgery Using the Da Vinci Surgical System: A Single Center Experience," Korean Journal of Thoracic and Cardiovascular Surgery, 2015, vol. 48, pp. 99-104.
Kong et al. "Da Vinci Tool Torque Mapping over 50,000 Grasps and its Implications on Grip Force Estimation Accuracy," 2018 International Symposium on Medical Robotics (ISMR), 2018, 6 pages.
Kumar et al. "Emerging role of robotics in urology," Journal of Minimal Access Surgery, Oct. 2005, vol. 1, No. 4, pp. 202-210.
Li et al. "Design of a Multi-Arm Surgical Robotic System for Dexterous Manipulation," Journal of Mechanisms and Robotics, Dec. 2016, vol. 8, article 061017, 10 pages.
Seibold "An Advanced Force Feedback Tool Design for Minimally Invasive Robotic Surgery," Technische Universität München, May 15, 2012, Doctoral Engineers dissertation, 218 pages.
Staub "Micro Endoscope based Fine Manipulation in Robotic Surgery," Technische Universitat Munchen Lehrstuhl Robotic und Echtzeitsysteme, Dissertation, Apr. 2013, 146 pages.
Tian et al. "A Robot-Assisted Surgical System Using a Force-Image Control Method for Pedicle Screw Insertion," PLOS One, Jan. 2014, vol. 9, No. 1, article e86346, 9 pages.
Vivek et al. "Study of Neuroarm and Force Sensing Grippers in Robo-Assisted Neurosurgery," International Journal of Current Engineering and Technology, Mar. 2016, Special Issue 4, pp. 444-447.

(56) References Cited

OTHER PUBLICATIONS

International Search Report and Written Opinion for International (PCT) Patent Application No. PCT/US2021/035667, dated Sep. 23, 2023, 16 pages.
International Search Report for PCT/IL2021/050804 date of completion is Oct. 8, 2021 (3 pages).
Official Action with English Summary for China Patent Application No. 202180046779.9, dated Jul. 12, 2025, 20 pages.

* cited by examiner

TIME-SPACED ROBOTIC REFERENCE FRAMES

CROSS-REFERENCE TO RELATED APPLICATIONS

This application is a National Stage Application of PCT/IL2021/050804 filed Jun. 30, 2021, which claims benefit of and priority to U.S. Provisional Application No. 63/046,393 filed Jun. 30, 2020, and the disclosures of each of the above-identified applications are hereby incorporated by reference in their entirety.

FIELD

The present technology generally relates to robotic surgery, and relates more particularly to navigation during robotic surgery.

BACKGROUND

Surgical navigation systems are used to track the position of one or more objects during surgery. Surgical robots are useful for holding one or more tools or devices during a surgery, and may operate autonomously (e.g., without any human input during operation), semi-autonomously (e.g., with some human input during operation), or non-autonomously (e.g., only as directed by human input).

SUMMARY

A robotic navigation system according to embodiments of the present disclosure comprises: a robot base; a robotic arm comprising a proximal portion secured to the robot base, a distal portion movable relative to the proximal portion, and a tracking marker secured to the robotic arm proximate the distal portion; at least one processor; a navigation system including a tracking marker sensor configured to identify positions of the tracking marker in a first coordinate space; and a memory. The memory stores instructions for execution by the at least one processor that, when executed, cause the at least one processor to: cause the robotic arm to move to a plurality of different poses; receive information relating to a position of the tracking marker in a second coordinate space when the robotic arm is in each of the plurality of different poses; and compare the positions of the tracking marker in the first coordinate space to the positions of the tracking marker in the second coordinate space.

The plurality of different poses may create a time-spaced robotic reference frame. At least one of the plurality of different poses may correspond to a maximum extension of the robotic arm. Each tracking marker may be configured to emit or reflect light through a covering. The tracking marker may be a first tracking marker configured to emit or reflect light with a first wavelength, and the robotic arm may comprise a second tracking marker configured to emit or reflect light with a second wavelength that is different than the first wavelength. The tracking marker may be a first tracking marker configured to emit light in pulses at a first frequency, and the robotic arm may comprise a second tracking member configured to emit light in pulses at a second frequency that is different than the first frequency. The robotic arm may be a first robotic arm, the tracking marker may be a first tracking marker, the robotic navigation system may further comprise a second robotic arm that includes a second tracking marker, the navigation system may be configured to identify positions of the second tracking marker in the first coordinate space, and the memory may include instructions for execution by the at least one processor that, when executed, cause the at least one processor to compare the positions of the second tracking marker in the first coordinate space to positions of the second tracking marker in the second coordinate space.

The robotic arm may be a first robotic arm, the tracking marker may be a first tracking marker, the robotic navigation system may further comprise a second robotic arm that includes a second tracking marker; the navigation system may be configured to identify positions of the second tracking marker in a third coordinate space different than the first coordinate space and the second coordinate space; and the memory may include instructions for execution by the at least one processor that, when executed, cause the at least one processor to compare the positions of the second tracking marker in the first coordinate space to positions of the second tracking marker in the third coordinate space.

The navigation system may be configured to detect a first position of the tracking marker at a first time when the robotic arm is in a first pose of the plurality of different poses, and to detect a second position of the tracking marker at a second time when the robotic arm is in a second pose of the plurality of different poses, the second time after the first time and the second position different than the first position. The memory may store additional instructions for execution by the processor that, when executed, cause the at least one processor to register the first coordinate space to the second coordinate spaced based at least on the detected first position, the detected second position, and the information. The received information may be obtained independently of the tracking marker sensor.

A method of utilizing a time-spaced robotic reference frame according to another embodiment of the present disclosure comprises: receiving, from a tracking marker sensor, first information about positions of a tracking marker over a plurality of different times, the tracking marker secured to a robotic arm of a robot and the first information collectively defining a unique shape in a navigation coordinate system; receiving, from a robotic system, second information corresponding to positions of the tracking maker in a robotic coordinate system at the plurality of different times; and comparing the robotic coordinate system to a navigation coordinate system based on the first information and the second information.

The robotic system may be configured to move the robotic arm to a first pose at a first one of the plurality of different times. The first pose may correspond to an extension of the robotic arm in a first direction, the robotic system may be configured to move the robotic arm to a second pose at a second one of the plurality of different times, and the second pose may correspond to an extension of the robotic arm in a second direction different than the first direction. The first direction may be orthogonal to the second direction. Each of the plurality of different times may occur during a continuous movement of the robotic arm. Comparing the robotic coordinate system to the navigation coordinate system based on the first information and the second information may include registering the robotic coordinate system to the navigation coordinate system. The registering may not be based on any information about any tracking marker not fixed to the robotic arm. The second information may comprise information about a position at which each tracking marker is fixedly secured to the robotic arm. The method may further comprise operating the robot based on the comparison.

A device for surgical navigation utilizing a time-spaced robotic reference frame according to another embodiment of the present disclosure comprises: at least one communication interface for receiving information from a robot; at least one tracking marker sensor configured to detect a tracking marker on a robotic arm of the robot; at least one processor; and at least one memory. The at least one memory stores instructions for execution by the at least one processor that, when executed, cause the at least one processor to: receive, from the robot, information corresponding to a pose of the robotic arm at each of a plurality of different times; receive, from the at least one tracking marker sensor, data corresponding to a detected position of the tracking marker at each of the plurality of different times; and combine the information and the data to generate a custom, time-spaced reference frame.

The at least one memory may store additional instructions for execution by the at least one processor that, when executed, further cause the at least one processor to confirm a position of an object in a predetermined coordinate space based on creation of the custom, time-spaced reference frame. The at least one memory may store additional instructions for execution by the at least one processor that, when executed, further cause the at least one processor to determine the pose of the robotic arm at each of the plurality of different times in which each pose is configured to avoid collisions with external objects near the robotic arm. The at least one tracking marker sensor may be configured to detect a tracking marker on each of a plurality of robotic arms, the information may correspond to a pose of each of the plurality of robotic arms at each of the plurality of different times, and the data may correspond to a detected position of the tracking marker at each of the plurality of different times. The information may correspond to a predicted pose of the robotic arm at each of the plurality of different times.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
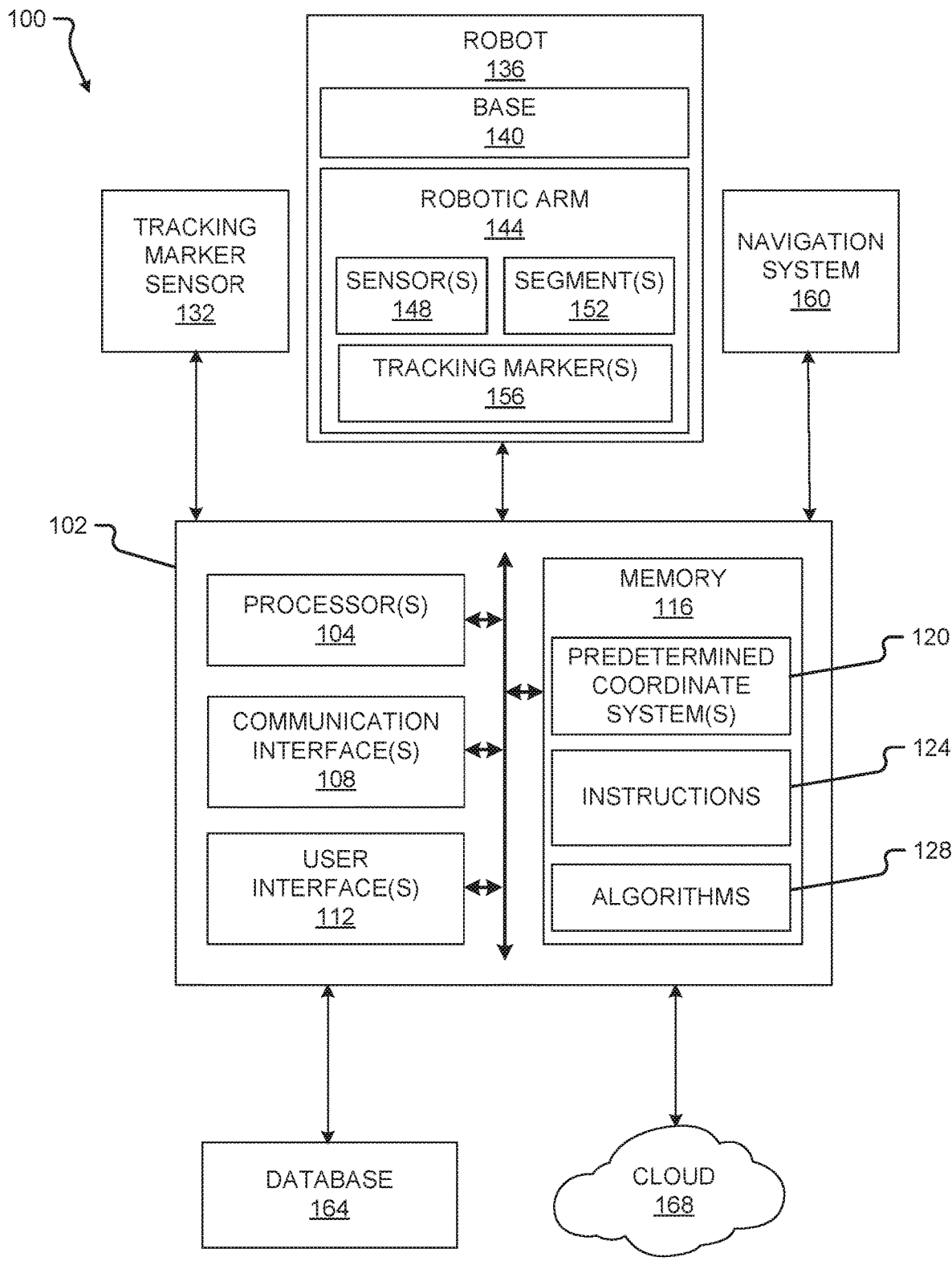
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Navigated robotic procedures often involve reference frames and trackers whose positions are detected by a tracking marker sensor. For example, a navigation system could use a camera as a tracking marker sensor, which can detect optical tracking markers on a reference frame attached to a robotic arm. With this information, the coordinate system of the robotic system can be correlated to the coordinate system of the navigation system. In other circumstances, the information from the tracking marker sensor, which can accurately determine the position and orientation of the robotic arm, can be used to calibrate the robotic system.

Larger reference frames provide better accuracy for navigated systems. However, large reference frames obstruct the operation field, are cumbersome, and are less stable. As disclosed herein, a robotic arm could create a time-spaced reference frame by moving to several different poses, pausing at each pose for a navigation camera or other tracking marker sensor to capture the pose of the robotic arm (e.g., the position of a tracking marker secured to the robotic arm). The points are then stored and combined, and after several movements (e.g., four), the stored points create a "time-spaced" frame—as if the navigation system saw a giant reference frame with reflective spheres or LEDs at those stored points.

In embodiments of the present disclosure, a robotic arm can quickly and accurately move to specified poses within robotic space. To translate these poses in robotic space into points in navigation space, a small reference frame could be attached to the robotic arm. However, for greater accuracy, the robotic arm could trace a "giant" reference frame by moving to multiple (e.g., four) specific locations (reference points), pausing at each location for the navigation camera to "capture" that reference point in navigation space. For example, the end of the robotic arm could have an LED (including, for example, an infrared emitting device), reflective sphere, optical pattern (e.g., a QR code, a bar code), a shape (e.g., a triangle, circle, square) (which may be printed or painted on the arm, applied as a sticker, or provided in any other manner), a color, an emitter of a particular wavelength, a reflector of a particular wavelength, an emitter that pulses at a particular frequency, or any other tracking marker for the camera or other tracking marker sensor to see and track. As the robot moves the robotic arm through the four poses in robotic space, the navigation system detects the tracking marker and thus identifies four corresponding reference points in navigation space, such that those four reference points effectively serve as a giant reference frame linking the robotic and navigations spaces.

Other embodiments may use multiple LEDs, reflective spheres, or other tracking markers on the robotic arm (so that the camera or other tracking marker sensor can track the robotic arm from multiple angles). In addition, the robotic arm could continuously move to and from a central point to each of the designated reference points, with the navigation camera continually tracking the tracking marker and thus the robotic arm, and detecting changes in direction (e.g., a 180-degree change from the arm moving to the reference point vs away from the reference point) to decrease the required time needed to form the time-spaced robotic reference frame.

U.S. patent application Ser. No. 16/244,369, entitled "System and Method for Registration Between Coordinate Systems and Navigation," filed on Jan. 10, 2019, and incorporated by reference herein in its entirety, describes a dynamic snapshot tracking device that may be moved to a plurality of positions within a navigation volume and tracked at each of the plurality of positions. The plurality of positions may be used in concert to define a virtual snapshot tracking device that is larger than a single physical snapshot tracking device, and thus to achieve greater accuracy and less deviation than might otherwise be possible with a single physical snapshot tracking device.

A time-spaced robotic reference frame as described herein (and created using a robot and a tracking marker sensor) may be particularly useful when a position of the robot and is fixed relative to a position of the tracking marker sensor and vice versa. Where the position of the tracking marker sensor relative to the robot is not fixed, a physical reference frame may be used in conjunction with a time-spaced robotic reference frame as described herein. Alternatively, a time-spaced robotic reference frame can be generated in such a way that relative movement (or a chance of relative movement) between the tracking marker sensor and the robot is minimized, such as by capturing the various points of the time-spaced robotic reference frame over a short period of time.

Turning first to FIG. 1, a block diagram of a system 100 according to at least one embodiment of the present disclosure is shown. The system 100 may be used, for example: to carry out one or more aspects of one or more of the methods disclosed herein; for navigation purposes; for registration purposes; for calibration operations; to verify operational integrity of a navigation system (such as the navigation system 160) or of a robot (such as a robot 136); or for any other useful purpose. The system 100 comprises a computing device 102, a tracking marker sensor 132, a robot 136, a navigation system 160, a database 164, and a cloud 168. Notwithstanding the foregoing, systems according to other embodiments of the present disclosure may omit any one or more of the computing device 102, the tracking marker sensor 132, the robot 136, the navigation system 160, the database 164, and/or the cloud 168. Additionally, systems according to other embodiments of the present disclosure may arrange one or more components of the system 100 differently (e.g., one or more of the tracking marker sensor 132, the robot 136, and the navigation system 160 may comprise the components shown in FIG. 1 as being part of the computing device 102).

The computing device 102 comprises at least one processor 104, at least one communication interface 108, at least one user interface 112, and at least one memory 116. A computing device according to other embodiments of the present disclosure may omit one or both of the communication interface(s) 108 and the user interface(s) 112.

The at least one processor 104 of the computing device 102 may be any processor identified or described herein or any similar processor. The at least one processor 104 may be configured to execute instructions stored in the at least one memory 116, which instructions may cause the at least one processor 104 to carry out one or more computing steps utilizing or based on data received, for example, from the tracking marker sensor 132, the robot 136, the navigation system 160, the database 164, and/or the cloud 168.

The computing device 102 may also comprise at least one communication interface 108. The at least one communication interface 108 may be used for receiving image data or other information from an external source (such as the tracking marker sensor 132, the robot 136, the navigation system 160, the database 164, the cloud 168, and/or a portable storage medium (e.g., a USB drive, a DVD, a CD)), and/or for transmitting instructions, images, or other information from the at least one processor 104 and/or the computing device 102 more generally to an external system or device (e.g., another computing device 102, the tracking marker sensor 132, the robot 136, the navigation system 160, the database 164, the cloud 168, and/or a portable storage medium (e.g., a USB drive, a DVD, a CD)). The at least one communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 108 may be useful for enabling the device 102 to communicate with one or more other processors 104 or computing devices 102, whether to reduce the time needed to accomplish a computing-intensive task or for any other reason.

The at least one user interface 112 may be or comprise a keyboard, mouse, trackball, monitor, television, touchscreen, button, joystick, switch, lever, and/or any other device for receiving information from a user and/or for providing information to a user of the computing device 102. The at least one user interface 112 may be used, for example, to receive a user selection or other user input in connection with any step of any method described herein; to receive a user selection or other user input regarding one or more configurable settings of the computing device 102 and/or of another component of the system 100; to receive a user selection or other user input regarding how and/or where to store and/or transfer data received, modified, and/or generated by the computing device 102; and/or to display information (e.g., text, images) and/or play a sound to a user based on data received, modified, and/or generated by the computing device 102. Notwithstanding the inclusion of the at least one user interface 112 in the system 100, the system 100 may automatically (e.g., without any input via the at least one user interface 112 or otherwise) carry out one or more, or all, of the steps of any method described herein.

Although the at least one user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the computing device 102, while in other embodiments, the user interface 112 may be located remotely from one or more other components of the computer device 102.

The at least one memory 116 may be or comprise RAM, DRAM, SDRAM, other solid-state memory, any memory described herein, or any other tangible non-transitory memory for storing computer-readable data and/or instructions. The at least one memory 116 may store information or data useful for completing, for example, any step of the methods 200 or 300 described herein. The at least one memory 116 may store, for example, information about one or more predetermined coordinate systems 120 (e.g., information about a robotic coordinate system or space, information about a navigation coordinate system or space, information about a patient coordinate system or space); instructions 124 for execution by the at least one processor 104, for example to cause the at least one processor 104 to carry out one or more of the steps of the method 200 and/or of the method 300; and/or one or more algorithms 128 for use by the processor in carrying out any calculations necessary to complete one or more of the steps of the method 300, the method 600, and/or of the method 700, or for any other calculations. Such predetermined coordinate system(s) 120, instructions 124, and/or algorithms 128 may, in some embodiments, be organized into one or more applications, modules, packages, layers, or engines, and may cause the at least one processor 104 to manipulate data stored in the at least one memory 116 and/or received from or via another component of the system 100.

The tracking marker sensor 132 is operable to detect one or more tracking markers 156 (described below). The tracking marker sensor 132 may be, for example, an optical camera; an infrared camera; a 3D camera system; a stereoscopic vision system; another imaging device; an electromagnetic system; or any other sensor that can detect one or more tracking markers 156. The tracking marker sensor 132 may comprise a dedicated processor for executing instructions stored in a dedicated memory of the tracking marker sensor 132, or the tracking marker sensor 132 may simply be configured to transmit data collected therewith to the computing device 102 or to another component of the system 100. Although shown in FIG. 1 as being in communication only with the computing device 102, in some embodiments, the tracking marker sensor 132 may be in communication with any one or more of the computing device 102, the robot 136, the navigation system 160, the database 164, and/or the cloud 168. Also, in some embodiments, the computing device 102 may comprise the tracking marker sensor 132, while in other embodiments, the navigation system 160 may comprise the tracking marker sensor 132. In still other embodiments, the robot 136 may comprise the tracking marker sensor 132.

The tracking marker sensor 132 may be positioned directly above an operating table or portion thereof, or above and to one side of an operating table or portion thereof, or in another convenient position within an operating room or other room housing the robot 136. The tracking marker sensor 132 may be positioned at a location selected to provide the tracking marker sensor 132 with a clear and/or unobstructed view of the robotic arm 144 of the robot 136 (and thus of one or more tracking markers 156 fixedly secured to the robotic arm 144) during operation thereof. In some embodiments, the tracking marker sensor 132 is fixed, while in other embodiments, the tracking marker sensor 132 may be precisely movable (whether manually or automatically) in one or more directions.

In still other embodiments, a position and/or field of view of the tracking marker sensor 132 may be used to determine where a robotic arm 144 may be moved to generate a time-spaced robotic reference frame as disclosed herein. For example, a surgeon or other medical staff could place the tracking marker sensor 132 in a location that seems to work well for the operating room or other space in which the tracking marker sensor 132 is being used. The orientation and/or field of view of the tracking marker sensor 132 may then be determined (e.g., by taking some shots with the tracking marker sensor 132 and recognizing/tracking objects in the field of view, or otherwise), and used to define an area in which the robot 136 described below could move the robotic arm 144 to create a time-spaced robotic reference frame as described elsewhere herein. Based on constraints in the defined area, the shape and size of the time-spaced robotic reference frame may be defined.

The tracking marker sensor 132 may be configured to capture data regarding one or more sensed tracking markers 156 at a plurality of moments in time. For example, where the tracking marker sensor 132 is a camera, the tracking marker sensor 132 may be configured to capture a sequence of still images comprising one or more tracking markers 156. The tracking marker sensor 132 may be configured to capture such data at periodic intervals, or when commanded by a user (e.g., via a user interface 112), or upon a signal (generated either autonomously or in response to user input) from the computing device 102, the robot 136, and/or the navigation system 160.

The tracking marker sensor 132 may additionally or alternatively be operable to capture data corresponding to one or more tracking markers 156 continuously, in real-time. In such embodiments, the tracking marker sensor 132 may provide a stream of real-time sensor data to the computing device 102, which may continuously process the sensor data to detect a changing position of one or more tracking markers 156 therein. In some embodiments, the tracking marker sensor 132 may be a video camera configured to capture a series of video frames. The processor 104 of the computing device 102 (or any other processor) may then be used to recognize or otherwise detect the tracking markers 156 in each video frame, and/or to compare movement in the different video frames to identify or extrapolate a movement trajectory of the tracking marker 156.

In some embodiments, the tracking marker sensor 132 may comprise more than one tracking marker sensor 132.

One benefit of continuously or periodically tracking the position of a robotic arm such as the robotic arm 144, and more specifically of a tracking marker sensor 156 positioned on such a robotic arm, whether by capturing still images or video of the robotic arm 144 and/or of a tracking marker sensor 156 positioned thereon, is that a registration of robotic space to navigation space may be continuously or periodically confirmed. This advantageously enhances patient safety by reducing the likelihood that any surgical step will be performed without proper alignment between the robotic space and the navigation space, either or both of which may also be aligned to the patient space. Where a robot is capable of providing independent position information about the robotic arm to a processor 104, the processor 104 can compare the independent position information from the robot to position information obtained using the tracking marker sensor 132 to provide a redundant safety layer. Moreover, the generation of time-spaced robotic reference frames as disclosed herein may be accomplished while the robot 136 (including the robotic arm 144) performs its planned surgical movement, so that no additional movements or time are needed to confirm the registration during the surgery. Rather, the tracking marker sensor 132 may be used to capture still images or video (or to otherwise monitor the robotic arm 144 and/or the tracking marker sensor 156 thereon) during the surgery, as the robot 136 moves the robotic arm 144 to appropriate poses for carrying out each step of a surgical procedure. Taken together, the respective positions of the tracking marker 156 at each of the plurality of poses form a time-spaced robotic reference frame, as further described elsewhere herein. Moreover, in some embodiments, a surgical plan detailing the planned movements of the robot 136 (including the robotic arm 144 thereof) may be analyzed to identify when the robot 136 will be in the most effective poses for capturing a position of a tracking marker 156 for use in generating a time-spaced robotic reference frame as disclosed herein.

Figure 2A:
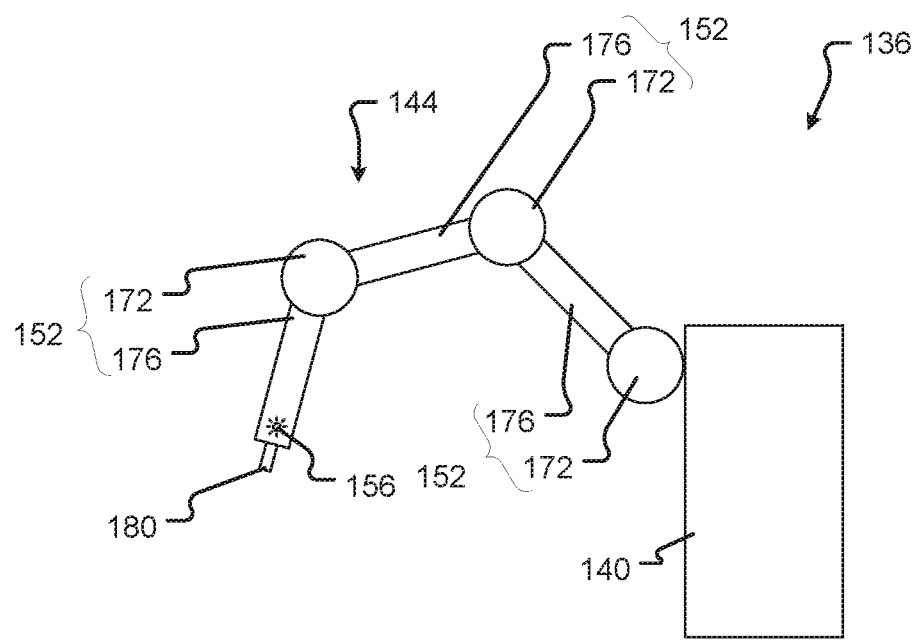
FIG. 2A depicts a robot according to at least one embodiment of the present disclosure.
Figure 2B:
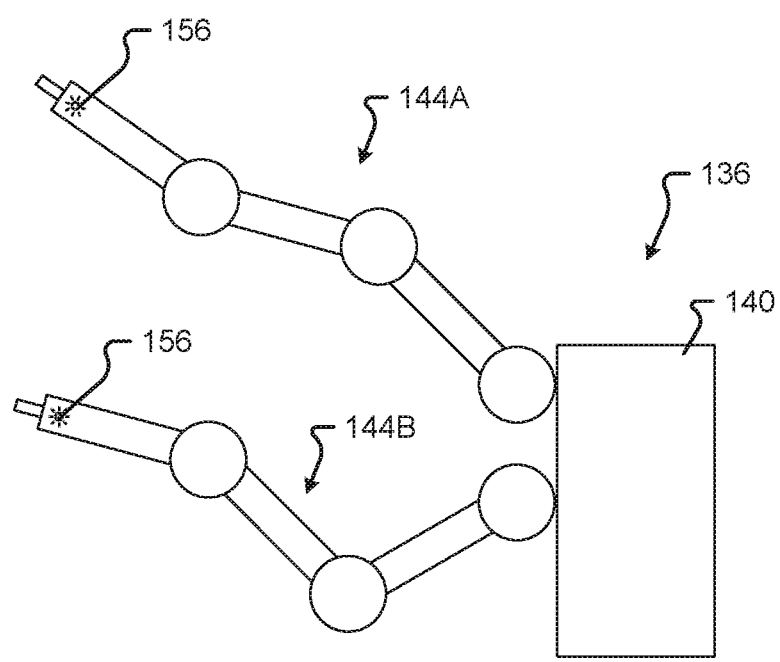
FIG. 2B depicts another robot according to at least one embodiment of the present disclosure.

With reference still to FIG. 1, and also to FIGS. 2A-2B, the robot 136 may be any surgical robot or surgical robotic system. The robot 136 may be or comprise, for example, the Mazor X™ Stealth Edition robotic guidance system. The robot 136 may comprise a base 140 that supports a robotic arm 144. The robot 136 may comprise one or more robotic arms 144. In some embodiments, such as that illustrated in FIG. 2B, the robotic arm 144 may comprise a first robotic arm 144A and a second robotic arm 144B. In other embodiments, the robot 136 may comprise more than two robotic arms 144. The robotic arm 144 may, in some embodiments, assist with a surgical procedure (e.g., by holding a tool in a desired trajectory or pose and/or supporting the weight of a tool while a surgeon or other user operates the tool, or otherwise) and/or automatically carry out a surgical procedure.

In embodiments of the present disclosure comprising a robot 136 with a plurality of robotic arms 144 (or a plurality of robots 136, each with one or more robotic arms 144), the robotic arms 144 may be used in combination to generate a time-spaced robotic reference frame. For example, each robotic arm 144 may assume and/or be moved to a unique pose, and a position of a tracking marker 156 on each robotic arm 144 may be detected and/or recorded. The resulting positions may then be used to generate a time-spaced robotic reference frame as described elsewhere herein. Alternatively, in some embodiments, one of a plurality of robotic arms may be used to generate a time-spaced robotic reference if or while another of the plurality of robotic arms (or a tracking marker 156 secured thereto) cannot be seen by the tracking marker sensor 132.

In some embodiments, a plurality of robotic arms 144 may share a common coordinate system or space, while in other embodiments, one or more robotic arms 144 may have a coordinate system or space that is different than a coordinate system or space used by another one or more robotic arms 144. In embodiments where the plurality of robotic arms 144 use a plurality of coordinate systems, at least one of the plurality of robotic arms 144 corresponding to each of the plurality of coordinate systems may be used to generate a time-spaced robotic reference frame that may then be used to map each coordinate system to a navigation coordinate system. Also in some embodiments, a distal end or end effector of one robotic arm 144 may be used to contact a designated location (e.g. a specific location on a patient) and another robotic arm 144 may be used to form a time-spaced robotic reference frame, thus allowing the reference frame to be used to con-elate patient space, robotic space, and navigation space.

Referring still to FIGS. 1 and 2A-2B, the robotic arm 144 may have three, four, five, six, or more degrees of freedom. The robotic arm 144 may comprise one or more segments 152. Each segment 152 may comprise a member 176 and a joint 172 to which the member 176 is attached and/or from which the member 176 extends. The joint 172 may be secured, for example, to the base 140 or to the member 176 of another segment 152. The joint 172 may be any type of joint that enables selective movement of the member 176 relative to the structure to which the joint 172 is attached. For example, the joint 172 may be a pivot joint, a hinge joint, a saddle joint, or a ball-and-socket joint. The joint 172 may allow movement of the member 176 in one dimension or in multiple dimensions, and/or along one axis or along multiple axes.

In embodiments of the robot 136 comprising a robotic arm 144 with only one segment 152, the joint 172 of the segment 152 may be secured to the base 140, and the member 176 of the segment 152 may comprise a proximal end secured to the joint 172 and a distal end supporting an end effector. The end effector may be, for example, a tool (e.g., a drill, saw, screwdriver, imaging device) or a tool guide (e.g., for guiding a biopsy needle, ablation probe, or other tool along a desired trajectory).

In embodiments of the robot 136 comprising a robotic arm 144 with a plurality of segments 152, such as that illustrated in FIG. 2A, a first segment 152 may comprise a joint 172 secured to the base 140, and the member 176 of the first segment 152 may comprise a proximal end secured to the joint 172 and a distal end supporting a joint of a second segment 152. The member 176 of the second segment 152 may comprise a proximal end secured to the joint 172 of the second segment 152, and a distal end supporting a joint 172 of a third segment 152, and so on. The member 176 of the final segment 152 may comprise a distal end that supports an end effector 180, which may be the same as or similar to the end effector described above. In such embodiments, the joints 172 of the various segments 152 may or may not be of the same type, and the members 176 of the various segments 152 may or may not be identical. In some embodiments, one or more of the members 176 may be configured to telescope or otherwise extend and retract for selective adjustment of a length thereof.

All or some of the joints 172 of the segments 152 of the robotic arm 144 may be powered (so as to be selectively controllable without physical manipulation by a human) Any one or more of electric, pneumatic, hydraulic, and/or other means may be used to selectively control movement of a member 176 about the joint 172. For example, each segment 152 may comprise a servo for selectively moving the member 176 of that segment 152 relative to the joint 172 of that segment 152.

The robotic arm 144 also comprises one or more sensors 148. Each sensor 148 may be positioned to detect a position of a member 176 of a given segment 152 relative to the joint 172 of the segment 152. For example, where the joint 172 of a given segment 152 is or comprises a hinge joint, a sensor 148 may detect an angular position of the member 176 relative to an axis of the hinge joint. Where the joint 172 of a given segment 152 is or comprises a rotary joint (e.g., configured to allow rotation of the member 176 about an axis that extends through the member 176 and the joint 172), the sensor 148 may detect an angular position of the member 176 relative to the axis that extends through the member 176 and the joint 172. Each sensor 148 may be, for example, a rotary encoder, a linear encoder, or an incremental encoder.

Data from the sensors 148 may be provided to a processor of the robot 136, to the processor 104 of the computing device 102, and/or to the navigation system 160. The data may be used to calculate a position in space of the robotic arm 144 relative to a predetermined coordinate system. For example, the robot 136 may calculate a position in space of the robotic arm 144 relative to a coordinate system with an origin at the position where the joint 172 of the first segment 152 of the robotic arm 144 is secured to the base 140. The calculation may be based not just on data received from the sensor(s) 148, but also on data or information (such as, for example, physical dimensions) corresponding to each segment 152 and/or corresponding to an end effector secured to the final segment 152. By way of example only, a known location of the proximal end of the robotic arm 144 (e.g., where a joint 172 of the first segment 152 is secured to the base 140), known dimensions of each segment 152, and data from the sensor(s) 148 about an orientation of the member 176 of each segment 152 relative to the joint 172 of each segment 152 may be used to calculate the path of the robotic arm through space.

Referring still to FIGS. 1A-1B, at least one tracking marker 156 is fixedly secured to or positioned on the robotic arm 144. The tracking marker 156 may be positioned, for example, proximate a distal end of the robotic arm 144, whether on an end effector 180 thereof or not. As used herein, "fixedly secured" does not mean "permanently secured," and indeed the tracking marker 156 may be detachable from the robotic arm 144. The tracking marker 156 may be an infrared emitting diode (IRED) or any other kind of light-emitting diode (LED). In some embodiments, the tracking marker 156 may be a reflective sphere, a geometric or optical pattern (such as, for example, a QR code or bar code). The tracking marker 156 may further be a shape (e.g., a triangle, circle, square) or a color, either of which may be printed or painted on the arm, applied as a sticker, or provided in any other manner. The tracking marker 156 may further be an emitter of a particular wavelength, a reflector of a particular wavelength, an emitter that pulses at a particular frequency, or another item or feature that may be readily distinguished by the tracking marker sensor 132. The tracking marker 156 may be configured to be detectable by a tracking marker sensor 132 even when covered by a drape or other covering that may be arranged on or over the robotic arm 144 to maintain a sterile operating room environment.

Where more than one tracking marker 156 is used (e.g., when a plurality of tracking markers 156 are secured to a single robotic arm 144, and/or when one or more tracking markers 156 are secured to each of a plurality of robotic arms 144), the tracking markers 156 may all be identical, or one or more of the tracking markers 156 may be different than another one or more of the tracking markers 156. In some embodiments, one or more of the tracking markers 156 may be configured to emit light at a first wavelength, and another one or more of the tracking markers 156 may be configured to emit light at a second wavelength different than the first wavelength. Also in some embodiments, one or more of the tracking markers 156 may be configured to reflect light at a first wavelength, while another one or more of the tracking markers may be configured to reflect light at a second wavelength that is different than the first wavelength. The emitted and/or reflected wavelengths of light of the embodiments described above may be wavelengths within a particular spectrum (e.g., wavelengths corresponding to red light versus wavelengths corresponding to blue light in the visible spectrum, or different wavelengths in the infrared spectrum) as well as wavelengths from different spectrums (e.g., a wavelength in the visible spectrum versus a wavelength in the infrared spectrum). Additionally or alternatively, one or more of the tracking markers 156 may be or comprise an emitter that pulses at a first frequency, and another one or more of the tracking markers 156 may be or comprise an emitter that pulses at a second frequency different than the first frequency.

In some embodiments, a plurality of tracking markers 156 may fixedly secured to, or positioned on, a segment 152 of the robotic arm 144 that comprises a distal end of the robotic arm 144 (but for, e.g., an end effector 180 that may be attached thereto). The plurality of tracking markers 156 may be arranged so that at least one tracking marker 156 is visible (e.g., to the tracking sensor 132) from any one of a plurality of possible orientations of the segment 152 and/or the arm 144. For example, in some embodiments, the tracking markers 156 may be circumferentially spaced about the robotic arm 144 proximate the distal end thereof.

In some embodiments of the present disclosure, a tracking marker 156 may be moveably secured to the robotic arm 144, and may further be selectively moveable relative to the robotic arm 144. In such embodiments, the tracking marker 156 may be configured to move (or to be moved automatically) from a first position on the robotic arm 144 (e.g., proximate a distal end thereof) to a second position on the robotic arm 144 (e.g., proximate a proximal end thereof) when the robotic arm 144 moves into or out of a certain position or set of positions. The purpose of such movement of the tracking marker 156 may be to facilitate maintenance of a line of sight between the tracking marker 156 and the tracking marker sensor 132, or to enable a plurality of positions of the tracking marker 156 to be recorded by the tracking marker sensor 132 without moving the robotic arm 144 itself. This may be advantageous, for example, to increase an effective size of a time-spaced robotic reference frame as described elsewhere herein. In such embodiments, the robot 136 (and/or another component of the system 100) may be configured to track whether the tracking marker 156 is in its respective first position or second position (or other position), and to provide such information to the navigation system 160 (or to any other component of the system 100) to enable con-elation of a robotic coordinate system with a navigation coordinate system based on a position of the tracking marker 156 relative to the robotic arm 144 as known by the robot 136 (and/or another component of the system 100), and further based on a position of the tracking marker 156 as detected by the navigation system 160 (e.g., using a tracking sensor 132). The robot 136 and/or another component of the system 100 may "know" the positions of the tracking marker 156 relative to the robotic arm 144 as a result of a calibration process, or simply by having stored in a memory thereof information corresponding to the positions of the tracking marker 156 relative to the robotic arm 144.

Referring again to FIG. 1, the navigation system 160 may provide navigation for a surgeon and/or for the robot 136 during an operation. The navigation system 160 may be any now-known or future-developed navigation system, including, for example, the Medtronic StealthStation™ S8 surgical navigation system. The navigation system 160 may include a camera or other sensor(s) for detecting and/or tracking one or more reference markers, navigated trackers, or other objects within an operating room or other room where a surgical procedure takes place. In some embodiments, the navigation system 160 may comprise the tracking marker sensor 132. In various embodiments, the navigation system 160 may be used to track a position of the robotic arm 144 (or, more particularly, of a tracking marker 156 attached to the robotic arm 144). The navigation system 160 may be used to track a position of one or more reference markers or arrays or other structures useful for detection by a camera or other sensor of the navigation system 160. The navigation system 160 may include a display for displaying one or more images from an external source (e.g., the computing device 102, tracking marker sensor 132, or other source) or a video stream from the camera or other sensor of the navigation system 160. In some embodiments, the system 100 may operate without the use of the navigation system 160.

The database 164 may store information that correlates the position and orientation, or pose, of the robotic arm 144 to a position of the tracking marker 156. The database 164 may also store information about each of a plurality of detected positions of a tracking marker 156. The database 164 may additionally or alternatively store, for example, information about or corresponding to one or more characteristics of the tracking marker 156; one or more surgical plans for use by the robot 136, the navigation system 160, and/or a user of the computing device 102 or of the system 100; one or more images useful in connection with a surgery to be completed by or with the assistance of one or more other components of the system 100; and/or any other useful information. The database 164 may be configured to provide any such information to the computing device 102 or to any other device of the system 100 or external to the system 100, whether directly or via the cloud 168. In some embodiments, the database 164 may be or comprise part of a hospital image storage system, such as a picture archiving and communication system (PACS), a health information system (HIS), and/or another system for collecting, storing, managing, and/or transmitting electronic medical records including image data.

The cloud 168 may be or represent the Internet or any other wide area network. The computing device 102 may be connected to the cloud 168 via the communication interface 108, using a wired connection, a wireless connection, or both. In some embodiments, the computing device 102 may communicate with the database 164 and/or an external device (e.g., a computing device) via the cloud 168.

Figure 3:
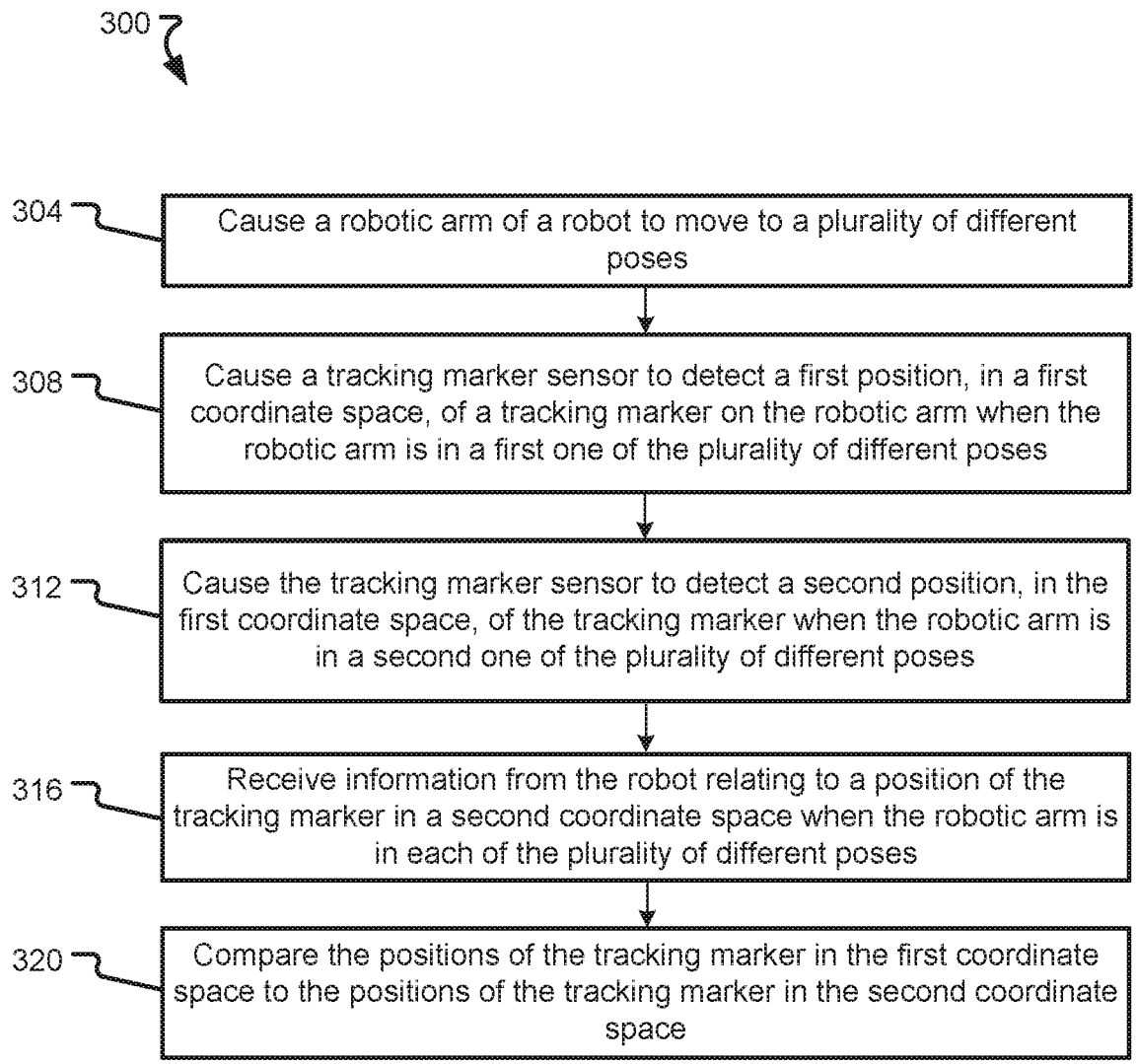
FIG. 3 is a flowchart of a method according to at least one embodiment of the present disclosure.
Figure 4C:
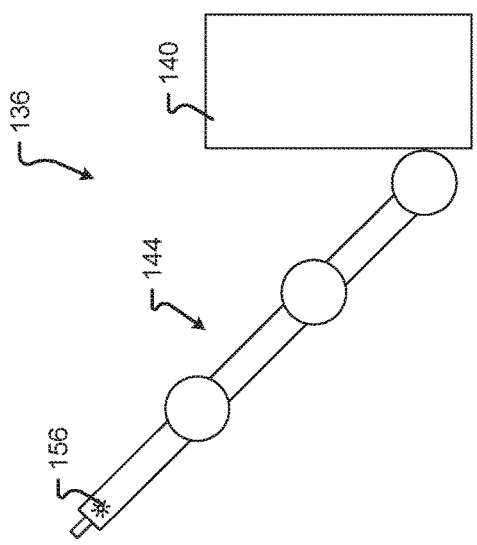
FIG. 4C depicts a field of view of a tracking marker sensor according to one embodiment of the present disclosure, with a robot within the field of view in a third pose.
Figure 4D:
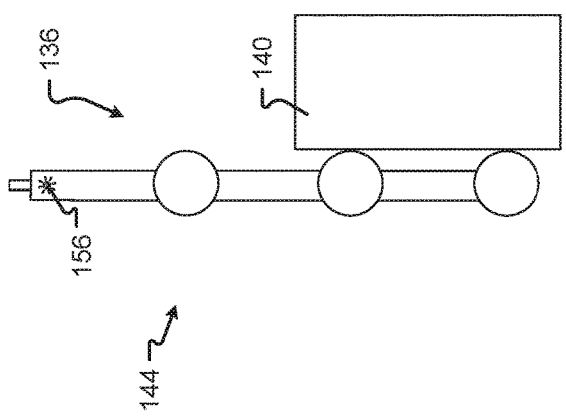
FIG. 4D depicts a field of view of a tracking marker sensor according to one embodiment of the present disclosure, with a robot within the field of view in a fourth pose.
Figure 4A:
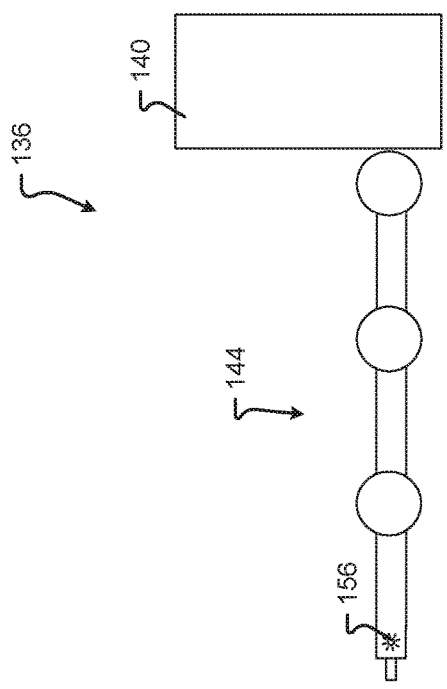
FIG. 4A depicts a field of view of a tracking marker sensor according to one embodiment of the present disclosure, with a robot within the field of view in a first pose.
Figure 4B:
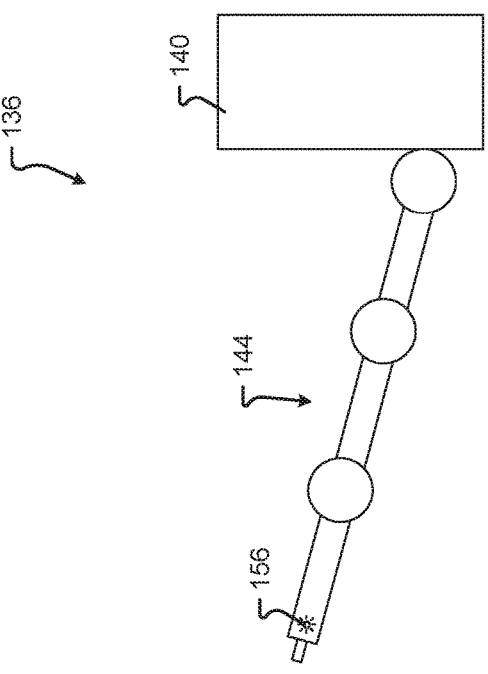
FIG. 4B depicts a field of view of a tracking marker sensor according to one embodiment of the present disclosure, with a robot within the field of view in a second pose.

Turning now to FIG. 3, a method 300 for utilizing a time-spaced robotic reference frame may be performed, for example, by at least one processor. The at least one processor may be the same as or similar to the processor(s) 104 of the computing device 102 described above. The at least one processor may be part of a robot (such as the robot 136) or part of a navigation system (such as the navigation system 160). A processor other than any processor described herein may also be used to execute the method 300. The at least one processor may perform the method 300 by executing instructions stored in a memory, such as the instructions 124 of the memory 116. The instructions may correspond to one or more steps of the method 300 described below. The instructions may cause the processor to execute one or more algorithms, such as the algorithms 128.

The method 300 comprises causing a robotic arm of a robot to move to a plurality of different poses (step 304). The robotic arm of the robot may be the same as or similar to the robotic arm 144 of the robot 136 described above. The plurality of different poses may be two poses, three poses, four poses, or more poses. In some embodiments, the plurality of different poses may comprise tens or hundreds of poses. The robotic arm of the robot is caused to move to the plurality of different poses in sequence, such that there is a space or period of time (whether measured in milliseconds, seconds, minutes, or otherwise) between a first time at which the robotic arm is in one of the plurality of different poses and a second time at which the robotic arm is in a subsequent one of the plurality of different poses. The space or period of time between any two poses of the plurality of different poses (provided the two poses are adjacent in time) may be identical, or may vary from one pair of adjacent-in-time poses to another pair of adjacent-in-time poses.

The plurality of different poses may be selected or determined to maximize a distance between a tracking marker on the robotic arm in each pose and the tracking marker on the robotic arm in every other pose. The plurality of different poses may alternatively be selected or determined to maximize a distance between the tracking marker on the robotic arm in each pose and the tracking marker on the robotic arm in every other pose while still ensuring that the tracking marker remains within a field of view of a tracking marker sensor, such as the tracking marker sensor 132. In still other embodiments, the plurality of different poses may be selected based at least in part on available poses within a navigation volume in light of one or more obstacles in the navigation volume (e.g., arms and hands of medical staff; tools, instruments, and other devices positioned within the navigation volume). In still further embodiments, the plurality of different poses may be selected based at least in part one or more of the foregoing considerations, and/or based on any other consideration.

In some embodiments, at least one of the plurality of different poses may be a pose in which the robotic arm is in contact with a designated location (e.g., a specific location on the patient). In such embodiments, the resulting time-spaced robotic reference frame may be used to con-elate patient space, robotic space, and navigation space.

FIGS. 4A to 4D illustrate, by way of example, one sequence of four different poses through which a robotic arm such as the robotic arm 144 may be caused to move. The robot 136 and robotic arm 144 thereof in FIGS. 4A-4D are shown in a field of view of a tracking marker sensor such as the tracking marker sensor 132. In the example of FIGS. 4A-4D, the robotic arm 144 is extended to or nearly to a maximum extension thereof in each of the four different poses shown in FIGS. 4A-4D. With the tracking marker 156 positioned proximate a distal end of the robotic arm 144 in FIGS. 4A-4D, extension of the robotic arm 144 to or nearly to a maximum possible extension beneficially enables the time-spaced robotic reference frame created as part of the method 300 to be as large as possible, thus facilitating improved accuracy relative to a smaller reference frame. In other embodiments, however, a robotic arm may not be extended to or nearly to a maximum extension thereof, whether in some or in all of the plurality of different poses. Although FIGS. 4A-4D illustrate a robotic arm 144 with a single tracking marker 156 affixed thereto, in some embodiments of the present disclosure, a plurality of tracking markers 156 may be affixed to the robotic arm 144.

In some embodiments, one of the plurality of different poses may be a current pose of the robotic arm, and another one of the plurality of different poses may be a pose of the robotic arm required in connection with a surgical step of a surgical procedure. The causing may comprise a processor (e.g., the processor 104) executing instructions stored in memory (e.g., the instructions 124 stored in the memory 116), which instructions may cause the processor to generate one or more signals and transmit the same to a robot such as the robot 136. The signal(s) may be sent, for example, via a communication interface such as the communication interface 108.

Referring again to FIG. 3, the method 300 also comprises causing a tracking marker sensor to detect a first position, in a first coordinate space, of a tracking marker on the robotic arm when the robotic arm is in a first one of the plurality of different poses (step 308). The tracking marker sensor may be the same as or similar to the tracking marker sensor 132. The tracking marker sensor may be an optical camera, an infrared camera, or any other sensor configured to detect the tracking markers. The tracking marker sensor, in some embodiments, may be part of a robot such as the robot 136, or part of a navigation system such as the navigation system 160, or part of a computing device such as the computing device 102. In some embodiments, the tracking marker sensor may be independent of any of the foregoing components, but may be in electronic communication with one or more of the foregoing components.

The detected position of the tracking marker may be defined based on a coordinate system such as a navigation coordinate system. The detected position of the tracking marker may be stored in a memory such as the memory 116, or in a database such as the database 164. The causing the tracking marker sensor to detect the first position may comprise a processor (e.g., the processor 104) executing instructions stored in memory (e.g., the instructions 124 stored in the memory 116), which instructions may cause the processor to generate one or more signals and transmit the signals to a tracking marker sensor such as the tracking marker sensor 132. The signal(s) may be configured to cause the tracking marker sensor to activate (e.g., to take a picture, to open an aperture) so as to detect the first position of the tracking marker. The signal(s) may be timed to cause the tracking marker to activate once the robotic arm has reached one of the plurality of different poses. In some embodiments, the signal(s) may cause the tracking marker sensor to activate periodically for a set number of iterations (e.g., 4 times, 10 times, 100 times) in a given period of time (e.g. 1 second, 4 seconds, 30 seconds, a minute), during which given period of time the robotic arm may be continuously moving through a plurality of different poses (e.g., without pausing at each pose). The signal(s) may be sent, for example, via a communication interface such as the communication interface 108.

The method 300 also comprises causing a tracking marker sensor to detect a second position, in the first coordinate space, of the tracking marker on the robotic arm when the robotic arm is in a second one of the plurality of different poses (step 312). The step 312 may be identical to or substantially the same as the step 308, but with the robotic arm in a second one of the plurality of different poses.

Although not reflected in FIG. 3, in some embodiments, the method 300 may comprise causing the tracking marker sensor to detect a third position, a fourth position, a fifth position, and so on of the tracking marker on each of the one or more robotic arms when the one or more robotic arms are in a third one, a fourth one, a fifth one, and so on, respectively, of the plurality of different poses. Each detected position of each tracking marker of the one or more robotic arms may be stored, for example, in a memory such as the memory 116 and/or in a database such as the database 164. When considered together, the various tracking marker positions define a time-spaced reference frame capable of having much larger dimensions than might otherwise be possible using, for example, a single, physical reference frame having a plurality of reflective spheres or other tracking markers secured to various fixed arms thereof. In some embodiments, the number of detected positions may be in the hundreds or greater.

Figure 5:
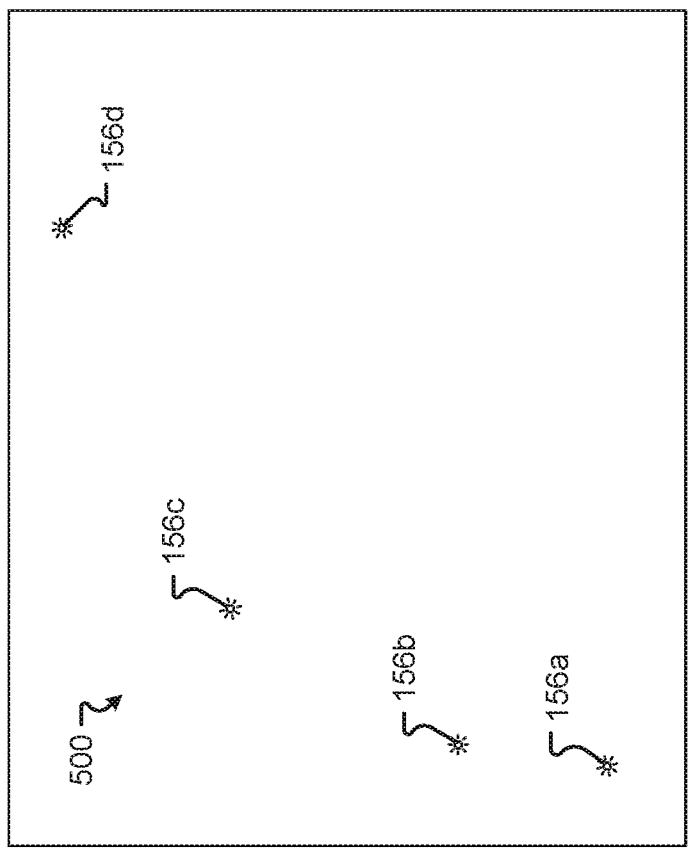
FIG. 5 depicts the detected position of a tracking marker at four separate times, corresponding to the four poses of the robot illustrated in FIGS. 4A-4D.

FIG. 5 shows an example of a time-spaced robotic reference frame 500 according to embodiments of the present disclosure. The time-spaced robotic reference frame 500 comprises four detected tracking marker positions. More specifically, the tracking marker 156a is shown in a first position (corresponding to the pose of the robotic arm 144 in FIG. 4A), which position was detected at a first time. The tracking marker 156b is shown in a second position (corresponding to the pose of the robotic arm 144 in FIG. 4B), which position was detected at a second time after the first time. The tracking marker 156c is shown in a third position (corresponding to the pose of the robotic arm 144 in FIG. 4C), which position was detected at a third time after the second time. The tracking marker 156d is shown in a fourth position (corresponding to the pose of the robotic arm 144 in FIG. 4D), which position was detected at a fourth time after the third time.

In embodiments of the present disclosure in which a robotic arm such as the robotic arm 144 comprises a plurality of tracking markers affixed thereto, a time-spaced robotic reference frame generated may be based on the detected positions of the plurality of tracking markers at each of a plurality of different times. Thus, for example, if the robotic arm 144 of FIGS. 4A-4D had two tracking markers 156 affixed thereto, and a tracking marker sensor were configured to detect both of the tracking markers 156 at each of the four different poses of the robotic arm 144, then the resulting time-spaced robotic reference frame would reflect eight tracking marker positions, rather than four tracking marker positions as in the reference frame 500. Inclusion of a plurality of tracking markers on a robotic arm may therefore reduce the number of different poses that a robotic arm must assume to obtain sufficient points for a time-spaced robotic reference frame. For example, if four points are needed for a given time-spaced robotic reference frame, and the robotic arm has two tracking markers affixed thereto, then the time-spaced robotic reference frame may be created by moving the robotic arm to only two different poses. Similarly, if 100 points are needed for a given time-spaced robotic reference frame, and the robotic arm has four tracking markers affixed thereto, then the time-spaced robotic reference frame may be created by moving the robotic arm to twenty-five different poses (rather than the fifty different poses that would be required if the robotic arm had two tracking markers secured thereto, or the 100 different poses that would be required if the robotic arm had only one tracking marker secured thereto).

The time-spaced robotic reference frame 500 corresponds somewhat to a physical reference frame having four reflective spheres or other tracking markers mounted thereto, except that the time-spaced robotic reference frame 500 is not constrained by the fixed dimensions of a physical reference frame. Indeed, a robot such as the robot 136, with a robotic arm such as the robotic arm 144, can define a time-spaced robotic reference frame such as the reference frame 500 on demand, using a plurality of different poses that may be identical to or different than any previous plurality of different poses. Indeed, a time-spaced robotic reference frame according to embodiments of the present disclosure may be formed by causing a robotic arm to move to a plurality of different poses selected based upon, for example, the position of other objects in the surgical environment. As a result, whereas use of a physical reference frame with fixed dimensions in a crowded surgical environment may require moving one or more tools, instruments, monitors, or other objects out of the way, a time-spaced robotic reference frame may be generated by causing a robotic arm to assume poses that avoid objects in the surgical environment, such that those objects need not be moved. In some embodiments, the poses to which a robotic arm moves to generate the time-spaced robotic reference frame may be selected or other determined, and/or a path between each such pose may be selected or otherwise determined, based on information in (or determined from) a surgical plan or elsewhere about the position of one or more objects in the navigation space. For example, based on a surgical plan that calls for the use of MIS towers in connection with a spinal surgery, the processor 104 or another processor may predict the position of the MIS towers based on information in the surgical plan and/or stored information about the dimensions of the MIS towers, and may determine one or more poses and/or paths to, from, and/or between the one or more poses in light of the predicted position of the MIS towers. In other embodiments, a processor 104 or another processor may use navigation information about the location of one or more tracked objects in the navigation space when determining one or more poses and/or paths to, from, and/or between the one or more poses for purposes described herein.

Additionally, time-spaced robotic reference frames as described herein need not always have the same pattern or dimensions. For example, one time-spaced robotic reference frame may have dimensions that correspond to a plurality of different poses that extend a robotic arm to or nearly to a maximum extension thereof for each pose, while another time-spaced robotic reference frame may have dimensions that correspond to a plurality of different poses where none of those poses require a maximum or near-maximum extension of the robotic arm.

Although the reference frame 500 is shown in two dimensions (e.g., all of the tracking markers 156a to 156d are positioned in the same plane), time-spaced robotic reference frames according to embodiments of the present disclosure may comprise tracking markers positioned in three dimensions. In other words, the plurality of different poses of the robotic arm may comprise poses that cause the tracking marker to be located at different X, Y, and Z positions relative to an origin of a robotic coordinate system, where X, Y, and Z represent orthogonal axes passing through the origin of the robotic coordinate system. Moreover, the tracking marker sensor may be capable of detecting a position of the tracking marker in three dimensions (e.g., in a navigation coordinate system).

A fourth dimension, time, is used to create the time-spaced robotic reference frame 500. However, the reference frame 500 itself, once generated by assembling or compiling the detected positions of the tracking marker 156 at each of the plurality of different poses corresponding to each of the plurality of different times, does not reflect time.

As evident from the foregoing, embodiments of the present disclosure advantageously eliminate a need for sometimes-bulky reference frames. For example, some navigation systems require certain minimum distances between tracking markers (or that physical references frames for holding tracking markers be a minimum size) to provide accurate navigation within a volume applicable to a given application. Larger volumes in particular may require larger reference frames than smaller volumes. In some instances, the reference frames holding tracking markers for surgeries or other medical procedures can extend from three inches to ten inches in multiple dimensions in order to achieve a minimum necessary size. As a result, these reference frames tend to be bulky, are easily bumped (which can, for example, cause undesired movement of the objects to which they are affixed), can get in the way of movement of a surgeon or of any movable object in an operating room environment, and can be difficult to use. The use of a time-spaced robotic reference frame as described herein enables a somewhat bulky object already in the operating room (the robot) to be used, when needed, to create a time-spaced reference frame, thus eliminating the need for dedicated reference frames and the problems associated therewith.

Returning to FIG. 3, the method 300 also comprises receiving information from the robot corresponding a position of the tracking marker in a second coordinate space when the robotic arm is in each of the plurality of different poses (step 316). Such information may be determined based on a sensed position of the robotic arm, as indicated by one or more sensors such as the sensors 148. Such information may also be determined based on a known relationship of a position of the robotic arm to a position of the tracking marker. Using the system 100 for an example, a tracking marker 156 may be secured to a precise location (e.g., a location on the robotic arm 144 that is precisely known, as reflected by coordinates and/or measurements relative to the robotic arm 144 or to a robotic coordinate system) proximate a distal end of a robotic arm 144. The precise location may be establishing during manufacture of the robotic arm 144 (e.g., precision tooling may be used to ensure the tracking marker 156 is installed precisely in a predetermined location on the robotic arm 144), or during a subsequent calibration process (e.g., the position of the tracking marker 156 relative to the robotic arm 144 and/or to a robotic coordinate system may be precisely measured after the tracking marker 156 has been affixed to the robotic arm 144).

In some embodiments, the information may not comprise a position of each tracking marker corresponding to each pose of the robotic arm, but may instead comprise information sufficient to determine or calculate a position of each tracking marker (in a robotic coordinate system) corresponding to each pose of the robotic arm. Thus, for example, the information may comprise information gathered from one or more sensors such as the one or more sensors 148 about the position and orientation of the robotic arm in each of the plurality of different poses, and/or information about the precise location of each tracking marker relative to the robotic arm. Based on such information, a processor such as the processor 104 may utilize one or more algorithms such as the algorithms 128 to calculate the position of each tracking marker in the robotic coordinate system for each pose of the plurality of different poses of the robotic arm. For example, if the information comprises sensor data sufficient to calculate a pose of one or more arm segments (e.g., segments 152) of a robotic arm such as the robotic arm 144, the calculated poses of the one or more arm segments may then be combined into a calculated pose of the robotic arm as a whole. Once the position of the robotic arm (in a robotic coordinate space) has been determined, then the position of the tracking marker can be determined based on a known position of the tracking marker relative to the robotic arm.

In some embodiments, the information received in the step 316 may comprise information stored in a memory such as the memory 116. Such information may include, for example, information about the dimensions, arrangement, range of motion, and/or other characteristics of the segment(s)s of the one or more robotic arms and/or of the one or more robotic arms as a whole.

The method 300 also comprises comparing the positions of the tracking marker in the first coordinate space to the positions of the tracking marker in the second coordinate space (step 320). The comparing may comprise registering the first coordinate space to the second coordinate space. The registering may comprise comparing the detected first position and the detected second position (both of which may be, for example, in a navigation coordinate space) to a received or calculated position of each tracking marker in a robotic coordinate space (as contained within or calculated from the received information), and based on the comparison, correlating the robotic coordinate space to the navigation coordinate space or vice versa.

In some embodiments, the registering may further be based on a detected position of a physical reference frame (e.g., not a time-spaced robotic reference frame), which may be secured to, for example, a robot base from which the robotic arm extends. The physical reference frame may be used to ensure that there is no relative movement between the tracking marker sensor and the robot base, whether during a period of time in which the robotic arm is caused to move to the plurality of different poses, during an entire surgical procedure, or during another period of time. Use of a physical reference frame on the robot base may be advantageous when the robot base is mounted on wheels or is otherwise movable. In other embodiments, however, the registering may be accomplished without information about or corresponding to any reference frame other than the time-spaced robotic reference frame. Such embodiments may include embodiments where the robot base and the tracking marker sensor are fixedly mounted relative to each other (e.g., by being fixedly mounted to a wall, a ceiling, an operating table, or other fixed structure). Such embodiments may also include embodiments where the plurality of different positions are reached during a relatively short period of time, such as a period of time equal to or less than five seconds, or equal to or less than three seconds, or equal to or less than two seconds, or equal to or less than one second.

In some embodiments, the registering may be accomplished without information about or corresponding to any reference frame other than the time-spaced robotic reference frame when the points making up the time-spaced robotic reference frame are captured within a predetermined period of time (e.g., within one second or less, or within two seconds or less, or within three seconds or less, or within five seconds or less), and with information about or corresponding to a physical reference frame attached to a robot base (or another physical reference frame) when the points making up the time-spaced robotic reference frame are captured in more than a predetermined period of time (e.g., in more than one second, or more than two seconds, or more than three seconds, or more than five seconds).

In other embodiments, the registering may be accomplished without use of or reliance upon any information corresponding to a physical reference frame (or any reference frame other than the time-spaced robotic reference frame), but only after an initial registration has been completed that is based, at least in part, on information about a physical reference frame. For example, if a physical reference frame is going to be obscured during a surgical procedure, then an initial registration can be accomplished using the physical reference frame, and re-registrations or registration verifications during the procedure may be accomplished using only the time-spaced robotic reference frame.

Also, when the comparison yields a conclusion that the detected tracking marker positions match the tracking marker positions as reflected by or determined using the information, the operational integrity of the robot and of the navigation system can be confirmed. This can be useful during surgical procedures as well as for initial calibration operations for the robotic system. On the other hand, if and when the comparison yields a conclusion that the detected tracking marker positions do not match the tracking marker positions as reflected by or determined using the information, a further conclusion can be reached that one or both of the robot and the navigation system lack operational integrity. Thus, when this occurs, a warning may be displayed to an operator of the robot and/or of the navigation system, and/or an audible sound may be played, via a user interface (such as, for example, the user interface 112 of the computing device 102, or a user interface specific to the robot or to the navigation system). Provision of such a warning to an operator of the robot and/or of the navigation system helps to ensure that the suspect operational integrity of the robot and/or of the navigation system can be investigated, and any errors corrected, before the robot and/or the navigation system are used further.

In some embodiments, where the detected tracking marker positions are only slightly different than the tracking marker positions as reflected by or determined using the information, the steps 304 through 316 may be repeated (e.g., based on a different plurality of different poses of the robotic arm), and the detected tracking marker positions may again be compared to the tracking marker positions as reflected by or determined using the information. If the second tracking marker positions are again only slightly different than the tracking marker positions as reflected by or determined using the information, then an error calculation and/or calibration process may be undertaken to determine an adjustment to be applied to in the future to ensure that the detected tracking marker positions match the tracking marker positions as reflected by or determined using the information, or vice versa. In other words, if an offset between a detected arrangement of the plurality of tracking markers and a corresponding set of tracking marker positions as reflected by or determined using the information can be characterized by a constant or a derived equation, such that the offset can be incorporated into further comparisons, then the operational integrity of the robot and/or of the navigation system may be confirmed.

The present disclosure encompasses embodiments of the method 300 that comprise more or fewer steps than those described above. Although aspects of the method 300 were described with respect to a single robot comprising a single robotic arm, the method 300 may utilize a single robot with a plurality of robotic arms (one or more of which having one or more tracking markers fixedly secured thereto), a plurality of robots each with a single robotic arm having one or more tracking markers fixedly secured thereto, and/or a plurality of robots each with a plurality of robotic arms (one or more of which having one or more tracking markers fixedly secured thereto).

Figure 6:
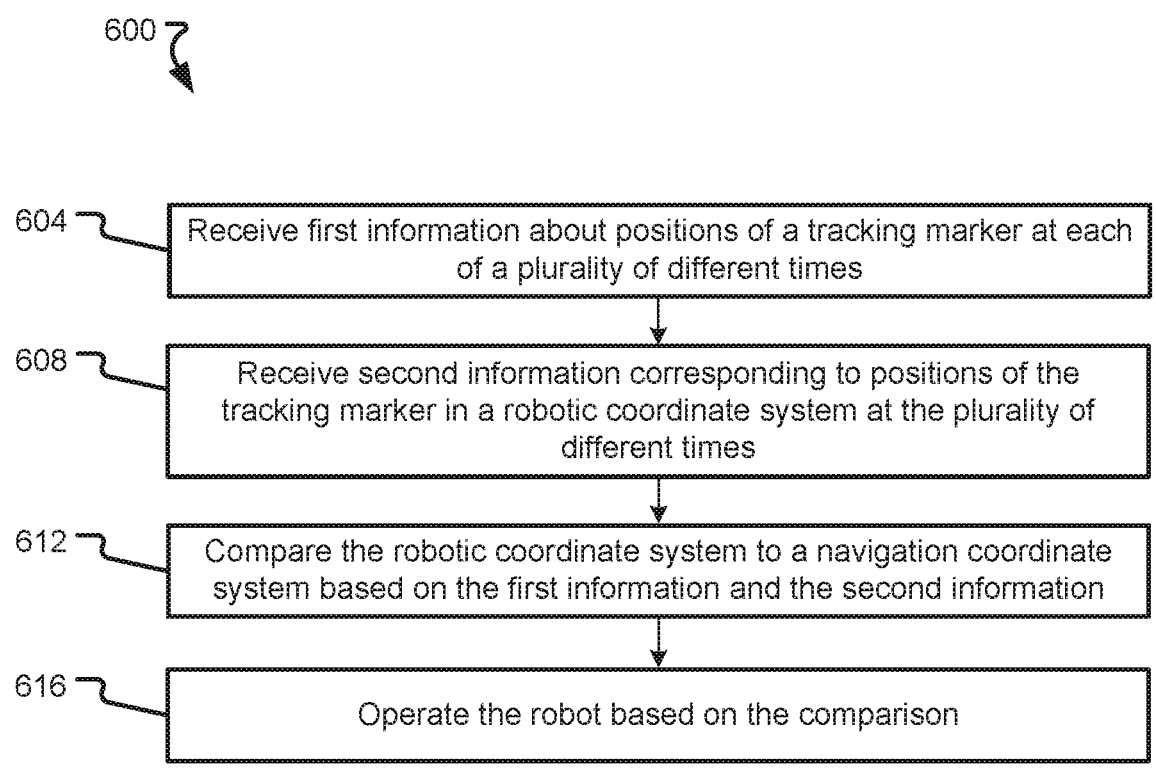
FIG. 6 is a flowchart of a method according to at least one embodiment of the present disclosure.

Turning now to FIG. 6, a method 600 of utilizing a time-spaced robotic reference frame for registration comprises receiving first information about positions of a tracking marker at each of a plurality of different times (step 304). The first information may be received, for example, from a sensor such as the tracking marker sensor 132, or any other sensor suitable for detecting the tracking marker. The first information may be received directly from the sensor or via one or more communication interfaces such as the communication interface 108, and/or via a cloud such as the cloud 168, or via any other network, device, or component.

The plurality of different times may comprise two times, three times, four times, or more times. In some embodiments, the plurality of different times may comprise ten times or 100 times. Each of the plurality of different times may fall within a period of time of one second or less, or five seconds or less, or ten seconds or less, or one minute or less, or more than one minute. The tracking marker may be, for example, a tracking marker 156, or any other tracking marker. The tracking marker may be fixedly secured to a robotic arm, which may be any robotic arm described herein, including, for example, a robotic arm 144 of a robot 136, or any other robotic arm.

The first information may be or comprise information about positions of the tracking marker in a navigation coordinate system at each of the plurality of times. In some embodiments, the first information may comprise information about a first position of the tracking marker in a navigation coordinate system at at least one time of the plurality of times, and may further comprise information about a second position of the at least one tracking marker relative to the first position. In other words, the first information may comprise information sufficient to determine a position of the tracking marker relative to a navigation coordinate system at each of the plurality of times.

The method 600 also comprises receiving second information corresponding to positions of the tracking marker in a robotic coordinate system at each of the plurality of different times (step 608). The second information may describe (or enable calculations sufficient to determine) the position of the tracking marker relative to a robotic coordinate space at each of the plurality of different times. The second information may be obtained, for example, from the robotic arm, which may be a robotic arm 144 as described herein or any other robotic arm. The second information may additionally or alternatively be obtained from or via a robot comprising the robotic arm, such as the robot 136, and/or from a memory such as the memory 116, a computing device such as the computing device 102 more generally, a database such as the database 164, a cloud such as the cloud 168, or another source.

The second information may be based, for example, on data obtained from one or more sensors in the robotic arm, such as the sensors 148. For example, the second information may comprise sensor data about a detected pose of one or more segments of the robotic arm and/or of the robotic arm as a whole. The second information may additionally or alternatively be based on one or more settings of one or more components of the robotic arm. For example, the second information may comprise data describing a position (whether an actual position or a commanded position) of one or more motors, servos, gears, or other devices or components used to control a pose of the robotic arm and/or one or more segments thereof. The second information may be obtained independently of the first information, and vice versa. The second information may comprise information describing the pose of the robotic arm at each of the plurality of times, or information from which the pose of the robotic arm at each of the plurality of times may be calculated. In the latter instance, one or more algorithms such as the algorithms 128 may be used to calculate the pose of the robotic arm at each of the plurality of times.

The second information may also comprise information about the position of the tracking marker relative to the robotic arm, and information about the robotic arm relative to the robotic coordinate system.

The method 600 also comprises comparing the robotic coordinate system to a navigation coordinate system based on the first information and the second information (step 612). The comparing may comprise registering the robotic coordinate system to the navigation coordinate system. The registering may be accomplished based on the first information and the second information. In some embodiments, the registering comprises correlating a pose of the robotic arm in the robotic coordinate system at each of the plurality of different times to a detected position of the tracking marker in the robotic coordinate system at each of the plurality of different times. Such correlating may comprise accessing information from a memory such as the memory 116, a database such as the database 164, a robot such as the robot 136, or another storage location. The accessed information may include, for example, information regarding a precise position of the tracking marker on the robotic arm, and/or information about the dimensions, arrangement, range of motion, and/or other characteristics of the segments of the robotic arm and/or of the robotic arm as a whole. Based on such information as well as information about a pose of the robotic arm in the robotic coordinate system (e.g., the second information received in step 608), a position of the plurality of tracking markers in the robotic coordinate system may be calculated. Such calculations may utilize, for example, one or more algorithms such as the algorithms 128. The result of the correlating may be a calculated or otherwise determined position, in the robotic coordinate system, of the tracking marker at each of the plurality of different times.

The registering may comprise determining a relationship between the robotic coordinate system and the navigation coordinate system based on a known position of the tracking marker in the navigation coordinate system (as included in or determined from the first information) at each of the plurality of different times and a known position of the tracking marker in the robotic coordinate system (as included in or determined from, e.g., the second information) at each of the plurality of different times. The registering may utilize one or more algorithms such as the algorithms 128 stored in the memory 116.

In some embodiments, the method 600 may also comprise registering a patient coordinate system to the navigation coordinate system. Where the robot is connected to the patient (as is sometimes the case during robotic or robotic-assisted surgery), or where the robotic coordinate system has already been registered to a patient coordinate system, registration of the robotic coordinate system to the navigation coordinate system (as described with respect to step 612 above) also enables registration of the patient coordinate system to the navigation coordinate system. In some embodiments, the registering comprises correlating the robotic coordinate system to a patient coordinate system (or vice versa), and, based on that registration, correlating the patient coordinate system to the navigation coordinate system. In other words, the registering may comprise determining a relationship between the patient coordinate system and the navigation coordinate system based on a relationship between the patient coordinate system and the robotic coordinate system and a relationship between the robotic coordinate system and the navigation coordinate system. Such registering may utilize one or more algorithms such as the algorithms 128 stored in the memory 116.

The method 600 also comprises operating the robot based on the comparison (step 616). The operating may comprise a processor such as the processor 104 executing instructions (e.g., instructions 124) stored in a memory such as the memory 116 that cause the processor 104 to transmit one or more signals to the robot 136 that cause the robotic arm 144 to move in one or more ways to carry out one or more steps of a surgical procedure. The comparison may beneficially enable the robotic arm to be moved to precise positions relative to a patient, using information about the patient such as one or more preoperative images and/or a preoperative surgical plan.

The present disclosure encompasses a number of variations on the method 600. For example, in some embodiments, the second information may comprise position information for the tracking marker (in the robotic coordinate system) at each of the plurality of times, such that the correlating described above with respect to the step 612 is unnecessary (as are any calculations to determine a pose of the robotic arm based on the second information, as described above with respect to the step 608). Additionally, while in the method 600 described above a position of the tracking marker in the robotic coordinate system at each of the plurality of different times is determined based on the second information about a pose of the robotic arm in the robotic coordinate system, in other embodiments a pose of the robotic arm may be determined based on the first information, and the registering step 612 may comprise registering the robotic coordinate system to the navigation coordinate system (or vice versa) based on the position of the robotic arm as determined from the first information and the position of the robotic arm as indicated by or determined from the second information.

The method 600 beneficially enables registration of a navigation coordinate system to a robotic coordinate system or vice versa without the use of a reference frame other than a time-spaced robotic reference frame formed (over time) by the robotic arm (including the tracking marker fixedly secured to the robotic arm) itself. The method 600 thus avoids the cost of a separate reference frame, the expenditure of the time needed to secure the separate reference frame to the robotic arm, and, in instances where the reference frame would be secured directly to the patient (e.g., to the patient's vertebra or pelvis), the incision that would otherwise be needed to secure the separate reference frame to the patient. Moreover, the method 600 removes the need for a snapshot frame that would otherwise be required during registration of a navigation coordinate system to a robotic coordinate system or vice versa.

The present disclosure encompasses embodiments of the method 600 with more or fewer steps than those described above.

Figure 7:
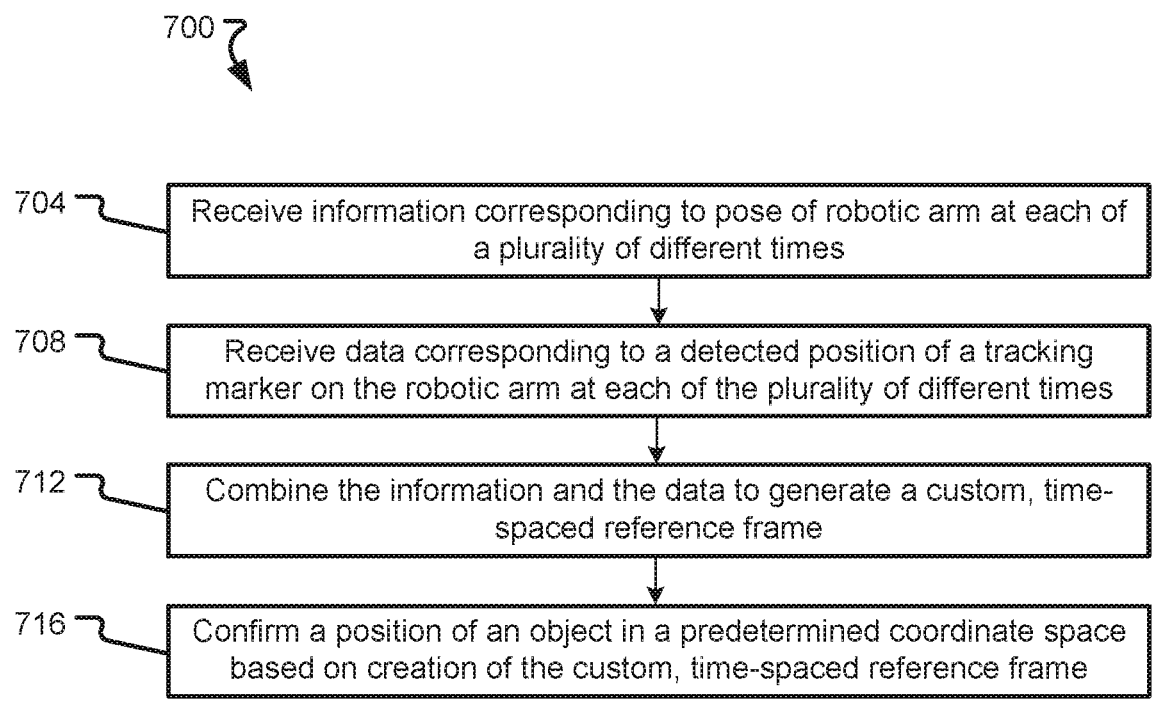
FIG. 7 is another flowchart of a method according to at least one embodiment of the present disclosure.

With reference now to FIG. 7, a method 700 of utilizing a robotic reference frame comprises receiving information corresponding to a pose of a robotic arm at each of a plurality of different times (step 404). The plurality of different times may comprise a first time and a second time after the first time. In some embodiments, the plurality of different times may further comprise a third time after the second time, a fourth time after the third time, a fifth time after the fourth time, and/or additional times. The plurality of different times may be evenly spaced (e.g., each time of the plurality of different times may be spaced from each adjacent time in the plurality of different times by the same amount of time), or differently spaced. The plurality of different times may all fall within a total time comprising one second less or less, ten seconds or less, one hundred seconds or less, one thousand seconds or less, or any other period of time. The plurality of different times may simply be determined by when the robotic arm reaches each of a plurality of different poses.

The robotic arm may be a robotic arm 144 as described herein, or any other robotic arm. A tracking marker is fixedly secured to the robotic arm proximate a distal end thereof. In some embodiments, more than one tracking marker may be fixedly secured to the robotic arm. Also in some embodiments, more than one robotic arm may be used in connection with the method 700. The pose of the robotic arm is different at each of the plurality of different times. The pose of the robotic arm at a first time of the plurality of different times may be such that the robotic arm extends substantially in a first direction, and the pose of the robotic arm at a second time of the plurality of different times may be such that the robotic arm extends substantially in a second direction that is orthogonal to the first direction In some embodiments, the pose of the robotic arm at a third time of the plurality of different times may be such that the robotic arm extends substantially in a third direction that is orthogonal to the first and second directions. In other embodiments, the robotic arm may not extend, in any of the poses corresponding to the plurality of different times, in any direction orthogonal or substantially orthogonal to any direction in which the robotic arm extends in any other pose corresponding to one of the plurality of different times.

In some embodiments, the information corresponding to a pose of the robotic arm at each of the plurality of different times may be information corresponding to a predicted pose of the robotic arm at each of the plurality of different times. For example, the information may correspond to a plurality of planned poses to which the robotic arm will be moved (e.g., in sequence, such that the robotic arm will assume each of the planned poses at a different time), and the plurality of different times may be determined by the times at which the robotic arm is predicted to reach each of the planned poses. The information may correspond to or comprise the results of one or more calculations carried out (e.g., by a robot such as the robot 136, or by a processor such as the processor 104) to determine a predicted position of a tracking marker based on an expected or current pose of the robotic arm to which the tracking marker is fixedly secured. At least one pose of the robotic arm at one of the plurality of different times may be a pose that enables an end of the robotic arm (whether an end effector or otherwise) to be in contact with an object, the position of which needs to be determined or confirmed (whether in a navigation coordinate space or otherwise). The information may comprise information about a position of a tracking marker fixedly secured to the robotic arm relative to a robotic coordinate system or another coordinate system. Where multiple robotic arms are used, each having a tracking marker fixedly secured thereto, the information may comprise information about a characteristic of each tracking marker, such as a wavelength, pulsating frequency, or geometric pattern of each individual tracking marker.

Each tracking marker may be any tracking marker described herein, including, for example, a tracking marker 156. Each tracking marker is secured to a robotic arm.

The method 700 also comprises receiving data corresponding to a detected position of a tracking marker on the robotic arm at each of the plurality of different times (step 708). The data may be received, for example, from a tracking marker sensor such as the tracking marker sensor 132. The data may comprise position information of the tracking marker in a navigation coordinate space or another coordinate space. Alternatively, the data may enable calculation of a position of the tracking markers in a navigation coordinate space or another coordinate space. Where multiple tracking markers are used, the data may comprise information about a characteristic of each individual tracking marker, such as a wavelength, pulsating frequency, or geometric pattern of each individual tracking marker.

Notably, the data corresponding to the detected position of the tracking marker is independent of the information corresponding to the pose of the robotic arm, even if such information comprises position information about the tracking marker. In other words, the data is generated without reference to the information, and the information is generated without reference to the data.

The method 700 also comprises combining the information and the data to generate a custom, time-spaced reference frame (step 712). The combination may yield, for example, a custom, time-spaced reference frame such as that shown in FIG. 5. When the detected position of the tracking marker at each of the plurality of different times (e.g., as reflected in the data) matches the predicted or expected position of the tracking marker (e.g., as reflected in or determined from the information), the exact coordinates of the custom, time-spaced reference frame are known in both a navigation coordinate system and a robotic coordinate system. As a result, the custom, one-time reference frame is usable instead of a separate reference frame that must be secured to or held by the robotic arm or another object or person.

The comparing may comprise using one or more algorithms such as the algorithms 128 to translate a position of the tracking markers in one coordinate system (e.g., in a robotic coordinate system) to a position of the tracking markers in another coordinate system (e.g., in a navigation coordinate system). The comparing may also comprise overlaying an image contained in or generated using the data corresponding to the detected positions of the tracking markers at the plurality of different times on a virtual image generated based on the information corresponding to the pose of the robotic arm at each of the plurality of different times to determine whether the tracking markers in both images line up with each other. Other comparison methods may also be used to determine whether the positions of the tracking marker as reflected in the data match the positions of the tracking marker as reflected in or determined from the information.

The method 700 also comprises confirming a position of an object in a predetermined coordinate space based on the creation of the custom, one-time reference frame (step 716). As noted above, when the positions of the tracking marker as reflected in or determined from the information match the positions of the tracking marker as reflected in the data, the precise coordinates of the time-spaced robotic reference frame are known. If the position (and, in some embodiments, the orientation) of an object can be detected simultaneously with the detection of the tracking marker at one or more of the plurality of different times, and/or if the robotic arm is in contact with a known surface or feature of the object at one or more of the plurality of different times, then the position (and, in some embodiments, the orientation) of the object may be determined using the custom, one-time reference frame, just as the position (and, in some embodiments, the orientation) of the object may be determined using a reference frame separate from the robotic arm.

The present disclosure encompasses embodiments of the method 700 with more or fewer steps than those described above.

Each of the embodiments described herein may utilize a single robotic arm with a single tracking marker secured thereto; a single robotic arm with a plurality of tracking markers secured thereto; a plurality of robotic arms with a single tracking marker secured to each robotic arm; and a plurality of robotic arms with a plurality of tracking markers secured to each robotic arm. As explained above, in embodiments that comprise or utilize a plurality of tracking markers, fewer different poses of the one or more robotic arms may be necessary to achieve a time-spaced robotic reference frame useable for an intended purpose. Similarly, in embodiments that comprise or utilize a plurality of robotic arms, each with at least one tracking marker secured thereto, fewer different poses of the plurality of robotic arms may be necessary to achieve a time-spaced robotic reference frame useable for an intended purpose.

Where a plurality of robotic arms are used in connection with any one or more of the systems, methods, or devices described herein, any information described above as corresponding to one or more poses of a robotic arm may comprise information corresponding to one or more poses of each robotic arm of the plurality of robotic arms. Such information may also be or comprise, in some embodiments, information about a position, in robotic coordinate space, of one or more tracking markers affixed to each of the plurality of robotic arm.

Embodiments of the present disclosure may beneficially increase patient safety during a surgical procedure. More specifically, a time-spaced robotic reference frame as disclosed herein may be used to confirm a registration between, for example, a robot coordinate space and a patient coordinate space, and/or between a navigation coordinate space and a robot coordinate space, and/or between a navigation coordinate space and a patient coordinate space (using a robotic coordinate space as an intermediary). For example, a robot coordinate space may be registered to a patient coordinate space using a relatively small physical reference frame, thus yielding a registration a first degree of accuracy. The robot coordinate space may also be registered to the patient coordinate space using a relatively larger time-spaced robotic reference frame, thus yielding a registration with a second degree of accuracy greater than the first degree of accuracy. As another example, after an initial registration of a robot coordinate space to a patient coordinate space, a time-spaced robotic reference frame as disclosed herein may be used at one or more times throughout a surgical procedure (or, in some embodiments, continuously throughout the surgical procedure) to confirm (using a navigation system comprising a tracking marker sensor) that a robotic arm is in fact in a position that that the robot understands the robotic arm to be in (e.g., through the use of one or more encoders or other sensors in the robotic arm).

Embodiments of the present disclosure enable a trade-off between use of space and time to maintain or improve the accuracy of a registration, re-registration, or registration verification (any one of which may be understood as a registration). For example, where available space is insufficient to utilize a physical reference frame of sufficient size to obtain a desired level of accuracy, a robotic arm having at least one tracking marker secured thereon, as described herein, may be used to generate, over time, a time-spaced robotic reference frame. On the other hand, where available space is sufficient to utilize a physical reference frame of sufficient size to obtain a desired level of accuracy, a single snapshot of such a reference frame may provide the needed information for the registration. The inclusion of multiple tracking markers on a single robotic arm (or of a single tracking marker on multiple robotic arms, or of multiple tracking markers on multiple robotic arms) may be used to reduce the amount of time needed to generate a time-spaced robotic reference frame, while increasing the amount of space needed. As space and/or time constraints change during the course of a surgical procedure, a reference frame suitable for the then-current constraints may be selected and used.

As may be appreciated based on the foregoing disclosure, the present disclosure encompasses methods with fewer than all of the steps identified in FIGS. 3, 6, and 7 (and the corresponding description of the methods 300, 600, and 700), as well as methods that include additional steps beyond those identified in FIGS. 3, 6, and 7 (and the corresponding description of the methods 300, 600, and 700). One or more aspects of the present disclosure may be the same as or similar to one or more corresponding aspects of the devices, systems, and methods disclosed in U.S. Patent Application Ser. No. 63/036,130, entitled "Robotic Reference Frames for Navigation" and filed on Jun. 8, 2020, the entirety of which is hereby incorporated by reference herein.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical robotic navigation system comprising:
   a robot base;
   a robotic arm comprising:
      a proximal portion secured to the robot base;
      a distal portion movable relative to the proximal portion; and
      a tracking marker secured to the robotic arm proximate the distal portion;
   at least one processor;
   a navigation system including a tracking marker sensor configured to identify positions of the tracking marker in a first coordinate space; and
   a memory storing instructions for execution by the at least one processor that, when executed, cause the at least one processor to:
      cause the robotic arm to move to a plurality of different poses;
      receive information relating to a position of the tracking marker in a second coordinate space when the robotic arm is in each of the plurality of different poses, wherein the navigation system is configured to detect a first position of the tracking marker at a first time during a surgical procedure when the robotic arm is in a first pose of the plurality of different poses, and to detect a second position of the tracking marker at a second time during the surgical procedure when the robotic arm is in a second pose of the plurality of different poses, and wherein at least one of the first pose and the second pose correspond to a pose in which the robotic arm is in contact with a designated location; and
      compare the positions of the tracking marker in the first coordinate space to the positions of the tracking marker in the second coordinate space.

2. The surgical robotic navigation system of claim 1, wherein the plurality of different poses creates a time-spaced robotic reference frame.

3. The surgical robotic navigation system of claim 1, wherein at least one of the plurality of different poses corresponds to a maximum extension of the robotic arm.

4. The surgical robotic navigation system of claim 1, wherein the robotic arm comprises a plurality of tracking markers secured thereto, wherein each tracking marker in the plurality of tracking markers is configured to emit or reflect light that is detectable by the tracking marker sensor.

5. The surgical robotic navigation system of claim 1, wherein the tracking marker is a first tracking marker configured to emit or reflect light with a first wavelength, and wherein the robotic arm comprises a second tracking marker configured to emit or reflect light with a second wavelength that is different than the first wavelength.

6. The surgical robotic navigation system of claim 1, wherein the tracking marker is a first tracking marker configured to emit light in pulses at a first frequency, and wherein the robotic arm comprises a second tracking member configured to emit light in pulses at a second frequency that is different than the first frequency.

7. The surgical robotic navigation system of claim 1, wherein the robotic arm is a first robotic arm, wherein the tracking marker is a first tracking marker, and wherein:
   the surgical robotic navigation system further comprises a second robotic arm that includes a second tracking marker;
   the navigation system is configured to identify positions of the second tracking marker in the first coordinate space; and
   the memory includes instructions for execution by the at least one processor that, when executed, cause the at least one processor to compare the positions of the second tracking marker in the first coordinate space to positions of the second tracking marker in the second coordinate space.

8. The surgical robotic navigation system of claim 1, wherein the robotic arm is a first robotic arm, wherein the tracking marker is a first tracking marker, and wherein:
   the surgical robotic navigation system further comprises a second robotic arm that includes a second tracking marker;
   the navigation system is configured to identify positions of the second tracking marker in a third coordinate space different than the first coordinate space and the second coordinate space; and
   the memory includes instructions for execution by the at least one processor that, when executed, cause the at least one processor to compare the positions of the second tracking marker in the first coordinate space to positions of the second tracking marker in the third coordinate space.

9. The surgical robotic navigation system of claim 8, wherein the second time is after the first time and the second position is different than the first position, wherein the designated location corresponds to a specific location on a patient, and wherein the third coordinate space comprises a patient space.

10. The surgical robotic navigation system of claim 9, wherein the memory stores additional instructions for execution by the processor that, when executed, cause the at least one processor to:
   register the first coordinate space to the second coordinate space and the third coordinate space based at least on the detected first position, the detected second position, the designated location, and the information.

11. The surgical robotic navigation system of claim 1, wherein the received information is obtained independently of the tracking marker sensor.

12. A method of surgical navigation utilizing a time-spaced robotic reference frame, comprising:
   receiving, from a tracking marker sensor, first information about positions of a tracking marker over a plurality of different times during a surgical procedure, the tracking marker secured to a robotic arm of a robot and the first information collectively defining a unique shape in a navigation coordinate system, wherein the robotic arm is in contact with a designated location for at least one time in the plurality of different times;
   receiving, from a robotic system, second information corresponding to positions of the tracking marker in a robotic coordinate system at the plurality of different times during the surgical procedure; and
   comparing the robotic coordinate system to a navigation coordinate system based on the first information and the second information, wherein comparing the robotic coordinate system to the navigation coordinate system based on the first information and the second information includes registering the robotic coordinate system to the navigation coordinate system.

13. The method of claim 12, wherein the robotic system is configured to move the robotic arm to a first pose at a first one of the plurality of different times, wherein the first pose corresponds to an extension of the robotic arm in a first direction, wherein the robotic system is configured to move the robotic arm to a second pose at a second one of the plurality of different times, and wherein the second pose corresponds to an extension of the robotic arm in a second direction different than the first direction.

14. The method of claim 13, wherein the first direction is orthogonal to the second direction.

15. The method of claim 12, wherein each of the plurality of different times occurs during a continuous movement of the robotic arm.

16. The method of claim 12, wherein the tracking marker sensor receives information about positions of a plurality of tracking markers over the plurality of different times, wherein the plurality of tracking markers are secured to the robotic arm of the robot.

17. The method of claim 16, wherein the registering is not based on any information about any tracking marker not fixed to the robotic arm.

18. The method of claim 12, wherein the second information comprises information about a position at which the tracking marker is fixedly secured to the robotic arm.

19. The method of claim 12, further comprising:
operating the robot based on the comparison.

20. A device for surgical navigation utilizing a time-spaced robotic reference frame, comprising:
at least one communication interface for receiving information from a robot;
at least one tracking marker sensor configured to detect a tracking marker on a robotic arm of the robot;
at least one processor; and
at least one memory storing instructions for execution by the at least one processor that, when executed, cause the at least one processor to:
receive, from the robot, information corresponding to a pose of the robotic arm at each of a plurality of different times during a surgical procedure, wherein the robotic arm is in contact with a designated location for at least one pose of the robotic arm;
receive, from the at least one tracking marker sensor, data corresponding to a detected position of the tracking marker at each of the plurality of different times during the surgical procedure; and
combine the information and the data to generate a custom, time-spaced reference frame.

21. The device of claim 20, wherein the at least one memory stores additional instructions for execution by the at least one processor that, when executed, further cause the at least one processor to:
confirm a position of an object in a predetermined coordinate space based on creation of the custom, time-spaced reference frame.

22. The device of claim 20, wherein the at least one memory stores additional instructions for execution by the at least one processor that, when executed, further cause the at least one processor to determine the pose of the robotic arm at each of the plurality of different times in which each pose is configured to avoid collisions with external objects near the robotic arm.

23. The device of claim 20, wherein the at least one tracking marker sensor is configured to detect a tracking marker on each of a plurality of robotic arms, the information corresponds to a pose of each of the plurality of robotic arms at each of the plurality of different times, and the data corresponds to a detected position of the tracking marker at each of the plurality of different times.

24. The device of claim 20, wherein the information corresponds to a predicted pose of the robotic arm at each of the plurality of different times.

* * * * *